US012232715B2

(12) United States Patent
Allard et al.

(10) Patent No.: US 12,232,715 B2
(45) Date of Patent: *Feb. 25, 2025

(54) SOFT TISSUE RETENTION DEVICE, INSTRUMENTATION AND RELATED METHODS

(71) Applicant: Paragon 28, Inc., Englewood, CO (US)

(72) Inventors: Randy Allard, Golden, CO (US); Shane Miller, Kilbeggan (IE); Douglas K. Blacklidge, Zionsville, IN (US)

(73) Assignee: Paragon 28, Inc., Englewood, CO (US)

( * ) Notice: Subject to any disclaimer, the term of this patent is extended or adjusted under 35 U.S.C. 154(b) by 1088 days.

This patent is subject to a terminal disclaimer.

(21) Appl. No.: 17/088,189

(22) Filed: Nov. 3, 2020

(65) Prior Publication Data

US 2021/0045732 A1 Feb. 18, 2021

Related U.S. Application Data

(63) Continuation of application No. PCT/US2019/030890, filed on May 6, 2019.
(Continued)

(51) Int. Cl.
*A61B 17/04* (2006.01)
*A61B 17/68* (2006.01)
(Continued)

(52) U.S. Cl.
CPC .. *A61B 17/0401* (2013.01); *A61B 2017/0409* (2013.01); *A61B 2017/044* (2013.01);
(Continued)

(58) Field of Classification Search
CPC .............. A61B 17/0401; A61B 17/683; A61B 17/8685; A61B 2017/044;
(Continued)

(56) References Cited

U.S. PATENT DOCUMENTS 5,707,373 A * 1/1998 Sevrain ................ A61B 17/688
411/338
5,893,850 A 4/1999 Cachia
(Continued)

FOREIGN PATENT DOCUMENTS

| FR | 2928824 | 9/2009 |
| WO | 2017127235 | 7/2017 |
| WO | 2019/213653 A1 | 11/2019 |

OTHER PUBLICATIONS

Extended European Search Report issued in European Patent Application No. 19796154.3, Jan. 7, 2022, 8 pages.
(Continued)

*Primary Examiner* — Nicholas W Woodall
(74) *Attorney, Agent, or Firm* — Heslin Rothenberg Farley & Mesiti P.C.

(57) ABSTRACT

Soft tissue retention devices, instrumentation and related methods are disclosed. The devices include a first member comprising a first head portion and a first threaded shaft portion extending from the first head portion that define a cannulated opening extending therethrough, and a second member comprising a second head portion and a second threaded shaft portion extending from the second head portion that define a cannulated opening that extends therethrough. The inner sides of the first and second head portions includes a row of teeth extending about the periphery thereof. The first head portion also includes a plurality of through holes positioned between the first threaded shaft portion and the row of teeth. The outer sides of the first and second head portions include non-circular drive openings. The instrumentation comprise a handle portion with a through aperture that allows for a user's finger to extend therethrough during an implantation procedure.

41 Claims, 42 Drawing Sheets

Related U.S. Application Data

(60) Provisional application No. 62/794,565, filed on Jan. 19, 2019, provisional application No. 62/666,918, filed on May 4, 2018.

(51) Int. Cl.
*A61B 17/86* (2006.01)
*A61F 2/08* (2006.01)

(52) U.S. Cl.
CPC ............... *A61B 2017/0445* (2013.01); *A61B 2017/0464* (2013.01)

(58) Field of Classification Search
CPC ..... A61B 2017/0445; A61B 2017/0464; A61F 2/0811
See application file for complete search history.

(56) References Cited

U.S. PATENT DOCUMENTS

| | | | |
|---|---|---|---|
| 5,980,526 A | 11/1999 | Johnson et al. | |
| 5,980,557 A | 11/1999 | Serin | |
| 6,050,819 A | 4/2000 | Robinson | |
| 6,231,606 B1 | 5/2001 | Graf | |
| 6,258,091 B1 | 7/2001 | Sevrain | |
| 6,302,887 B1 | 10/2001 | Spranza | |
| 6,383,187 B2 | 5/2002 | Tormala | |
| 6,464,713 B2 | 10/2002 | Bonutti | |
| 6,517,543 B1 | 2/2003 | Berrevoets | |
| 6,569,186 B1 | 5/2003 | Winters et al. | |
| 6,589,244 B1 | 7/2003 | Sevrain | |
| 6,648,890 B2 | 11/2003 | Culbert | |
| 6,918,912 B2 | 7/2005 | Seemann | |
| 7,074,203 B1 | 7/2006 | Johanson | |
| 7,578,825 B2 | 8/2009 | Huebner | |
| 7,604,659 B2 | 10/2009 | Lee | |
| 7,686,807 B2 | 3/2010 | Padget | |
| 7,833,255 B2 * | 11/2010 | Chow | A61B 17/683 606/300 |
| 8,043,347 B2 | 10/2011 | Jiang | |
| 8,147,514 B2 | 4/2012 | Bonutti | |
| 8,357,186 B2 | 1/2013 | Hadi | |
| 8,632,570 B2 | 1/2014 | Biedermann | |
| 8,672,985 B2 | 3/2014 | Chow | |
| 8,845,699 B2 | 9/2014 | Bonutti | |
| 8,858,634 B2 | 10/2014 | Lewallen | |
| 8,968,374 B2 | 3/2015 | Hoof | |
| 9,011,503 B2 | 4/2015 | Duggal | |
| 9,017,404 B2 | 4/2015 | Champagne | |
| 9,089,377 B2 | 7/2015 | Brown | |
| 9,247,963 B2 | 2/2016 | Kollmer | |
| 9,333,069 B2 | 5/2016 | Denham | |
| 9,445,842 B2 | 9/2016 | Cianfrani | |
| 9,510,883 B2 | 12/2016 | Weiss | |
| 10,231,767 B2 * | 3/2019 | Campbell | A61B 17/809 |
| 2002/0055743 A1 | 5/2002 | Seemann | |
| 2005/0240188 A1 | 10/2005 | Chow | |
| 2007/0250059 A1 * | 10/2007 | Weisshaupt | A61B 17/683 606/60 |
| 2009/0228049 A1 * | 9/2009 | Park | A61B 17/864 606/301 |
| 2011/0137356 A1 | 6/2011 | Kollmer | |
| 2011/0319925 A1 | 12/2011 | Helgerson | |
| 2014/0222087 A1 | 8/2014 | Greenberg | |
| 2016/0038186 A1 * | 2/2016 | Herzog | A61B 17/686 606/328 |
| 2016/0135861 A1 * | 5/2016 | Kollmer | A61B 50/20 606/324 |
| 2018/0055623 A1 * | 3/2018 | Blacklidge | A61B 17/7291 |

OTHER PUBLICATIONS

International Search Report and Written Opinion of the International Searching Authority for International Application No. PCT/US2019/030890 mailed on Jul. 18, 2019.

* cited by examiner

SOFT TISSUE RETENTION DEVICE, INSTRUMENTATION AND RELATED METHODS

CROSS REFERENCE TO RELATED APPLICATIONS

This application is a continuation of PCT/US2019/030890 filed on May 6, 2019 and entitled Soft Tissue Retention Device, Instrumentation and Related Methods, which claims priority benefit of U.S. Provisional Patent Application No. 62/666,918, filed May 4, 2018, and entitled Instrument and Method of Installing a Tendon Retention Device During a Tendon to Bone Attachment Procedure, and also claims priority benefit of U.S. Provisional Patent Application No. 62/794,565, filed Jan. 19, 2019, and entitled Soft Tissue Retention Device and Related Methods, which are hereby incorporated herein by reference in their entireties.

TECHNICAL FIELD

The present disclosure relates to surgical devices, implants, instrumentation, systems and related methods for retention of soft tissue to a bone, and more specifically to surgical devices, implants, instrumentation, systems and related methods for retention of soft tissue (e.g., tendons or ligaments) to a relatively small bone.

BACKGROUND

In some orthopedic procedures, it is necessary or desirable to attach or re-attach soft tissue (e.g., a tendon or a ligament) to a bone. This is typically accomplished by using an implant/device to physically secure the soft tissue to the bone. During the procedure, the surgeon or other user may utilize multiple instruments during the attachment procedure. These instruments typically require two-hands for engagement and use (e.g., manipulation to effectuate the procedure), which requires the user to constantly switch between different instruments that are not utilized simultaneously. It is difficult to correctly align soft tissue (e.g., a tendon or ligament) to an attachment bone while handling different implantation instruments, especially ones needing two-handed use. Current instruments and methods for attaching soft tissue to a bone are thereby lacking.

The extremities are an area of the body where soft tissue-to-bone attachment procedures are commonplace. One such area is the toes of the foot. For instance, the toes of the human foot commonly become contracted. The contraction of a toe produces pain due to increased pressure at the plantar metatarsal head, the dorsal proximal interphalangeal joint, and the distal end of the toe, for example. Procedures utilized to correct the deformity include tendon release, tendon transfer, partial joint (interphalangeal joint) resection (arthroplasty), and joint (interphalangeal joint) fusion (arthrodesis). For flexible deformities, tendon procedures are often utilized. With a reducible contracture of a toe, a transfer of the flexor digitorum longus tendon to the extensor tendon apparatus is often used with a variety of techniques. The contracted flexor digitorum longus tendon is released from its position on the base of the distal phalanx and it is transferred medial or lateral to the proximal phalanx and sutured to the extensor tendon apparatus dorsally with the tendon tensioned to correct the alignment of the toe. This releases the deforming force of the contracted flexor tendon on the interphalangeal joints while preserving the tendons ability to flex the metatarsophalangeal joint. Correcting the alignment can alleviate the pain associated with the contracture.

Current procedures are performed to facilitate a secure new position for the flexor digitorum longus tendon despite the new location being less than ideal. Procedures to transfer the flexor digitorum longus tendon within the toe typically have the goal of plantar flexing of the proximal phalanx at the metatarsophalangeal joint while releasing the contracture of the interphalangeal joints. Unfortunately, current procedures do not provide attachment of the flexor digitorum longus tendon to the plantar base of the proximal phalanx where it can best serve its new purpose. With attachment of the transferred flexor digitorum longus tendon to a location other than the plantar base of the proximal phalanx, metatarsophalangeal joint instability can persist, and transverse deviation of the toe can be exacerbated. The tendon is not routinely attached to its ideal new position due to technical difficulties and inadequate fixation methods.

During a direct repair of a plantar metatarsophalangeal joint capsule (plantar plate) rupture, the flexor digitorum longus tendon is often used to reinforce the repair. The tendon is secured to the plantar base of the proximal phalanx with transosseus suturing or a small tendon anchor. The bone of the proximal phalangeal base is small and using the currently available tendon suture anchors is difficult—especially considering the challenge of appropriately tensioning the tendon while trying to secure it into its new position with suture. The aging population and associated osteopenia adds to the difficulty of attaining secure tendon to bone fixation. Other than a direct plantar metatarsophalangeal joint ligament repair type procedure, most efforts to simply realign a contracted toe are from dorsal, so the plantar base of the proximal phalanx is not exposed. If a secure means of fixation for the flexor digitorum longus tendon under appropriate tension for correcting a contracted toe could be done efficiently, and reproducibly, the approach to reconstructing the common deformity could be vastly improved.

Many other deformities, conditions, injuries and other anatomical scenarios exist where it is desirable to attach/secure/fix soft tissue, such as but not limited to tendons or ligaments, to a bone, such as but not limited to a relatively small bone (e.g., a phalange, metatarsal or metacarpal).

Devices, implants, instrumentation, systems and related methods and methods that securely attach soft tissue (e.g., a tendon or ligament) to a bone, such as but not limited to a relatively small bone, are thus desirable. Further, devices, implants, instrumentation, systems and related methods that that attach soft tissue (e.g., a tendon or ligament) to a bone and act/function through the bone are also desirable. Further, devices, implants, instrumentation, systems and related methods that provide for a multi-function instrument that is usable with a single hand for implanting a tissue retention device are also desirable.

SUMMARY

The present disclosure is directed toward devices, implants, instrumentation, systems and related methods for retaining or coupling soft tissue (such as, but not limited to, tendons and ligaments) to bones (such as, but not limited to, relatively small bone (for example, bones of the foot and or hand). In some embodiments, the devices, implants, instrumentation, systems and related methods may be configured to couple the flexor digitorum longus tendon to the plantar aspect of a proximal phalangeal base for the correction of a toe contracture, for example. The devices, implants, instrumentation, systems and related methods provide for a secure retention, connection or coupling of the soft tissue to the bone. For example, the devices, implants, systems and related methods include locking teeth that resist de-coupling or backing out from the bone. The devices, implants, instrumentation, systems and related methods are also configured to act/function through the bone. Allowing the instrumentation to act through the bone facilities selection/configuration of an appropriately/selectively sized device/implant/system for a particular bone. Allowing the instrumentation to act through the bone also facilitates blind fitting and tightening of device/implant/system through the bone.

The devices, implants and systems of the present disclosure comprise a first component or member and a second component or member, the nomenclature first and second being arbitrary. The first component may be considered a tack member that directly couples with the soft tissue, while the second component may be considered an anchor member that directly couples with the bone. The tack member includes a head portion configured for press-fit or instrument aided reception into the soft tissue (and potentially adjacent bone) to retain the soft tissue against the adjacent bone. The head portion of the tack member may include a plurality of through apertures which allow the soft tissue to extend therein/therethrough when the device is tightened to the bone and soft tissue to exsanguinate and securely grip/couple the soft tissue. The anchor member also includes a head portion configured for press-fit or instrument aided reception into the bone. The head portion of the anchor member includes an anti-loosening feature or anti-loosening features such as, but not limited to, teeth, tangs and/or cutouts, that engage the bone to prevent the anchor member from backing out or working loose of the bone. The tack and anchor members each also include a stem portion that extend into an aperture extending through the bone and threadably mate/couple therein. The stem portion of the tack and anchor members may be central or centered on the head portion thereof. The tack and anchor members can thereby be introduced into the aperture of the bone from opposing sides One of the stem portions of the tack or anchor members comprises an externally threaded male component, and the stem portion of the other of the tack or anchor members comprises an internally threaded female component. The head and stem portions of both of the tack member and the anchor member are cannulated (such that the device/implant/system is cannulated as a whole) to allow the instrumentation to extend through in situ.

In broad terms, in some embodiments, the soft tissue retention devices, implants and systems comprise a headed tack member having a rough surface on the head portion surrounding a threaded shaft portion to engage soft tissue and extend into an aperture of a bone from a first side of the bone, and a headed anchor member having a rough surface on the head portion surrounding a threaded shaft portion to engage the bone and extend into the aperture of the bone from a second side of the bone, the threaded shaft portions configured to threadably mate/couple within the aperture of the bone, and the head and shaft portions of both the tack and anchor members being cannulated to allow instrumentation to extend through in situ.

In one aspect, the present disclosure provides a device for retaining soft tissue to a bone. The device comprises a first member comprising a first head portion and a first threaded shaft portion extending from an inner side of the first head portion, the first head portion and the first threaded shaft portion defining a cannulated opening that extends through the first member. The device also comprises a second member comprising a second head portion and a second threaded shaft portion extending from an inner side of the second head portion, the second head portion and the second threaded shaft portion defining a cannulated opening that extends through the second member. The inner side of the first head portion comprises a row of teeth extending about the periphery of the first head portion and a plurality of through holes positioned between the first threaded shaft portion and the row of teeth that extend to an outer side of the first head portion that opposes the inner side thereof. The outer side of the first head portion includes a first drive aperture that is non-circular in cross-section. The inner side of the second head portion comprises a row of angled teeth extending about the periphery of the second head portion and an outer side of the second head portion that opposes the inner side thereof includes a second drive aperture that is non-circular in cross-section.

In another aspect, the present disclosure provides a method for securing soft tissue to a bone. The method comprises forming an aperture in a portion of soft tissue, and forming a through aperture in a bone. The method also comprises obtaining the device for retaining soft tissue to a bone described immediately above. The method further comprises extending the first threaded shaft portion of the first member of the device through the aperture in the soft tissue and into the through aperture of the bone with the inner side of the first head portion of the device in engagement with the soft tissue. The method also comprises extending the second threaded shaft portion of the second member of the device into the through aperture of the bone with the inner side of the second head portion of the device in engagement with the bone. The method further comprises threadably coupling the first and second shaft portions together within the through aperture of the bone. The method also comprises compressing the first head member against the soft tissue and the second head member against the bone.

In another aspect, the present disclosure provides a system for securing soft tissue to a bone. The system comprises the device for retaining soft tissue to a bone described above. The system also comprises a first instrument comprising a guide wire portion extending from a first drive projection provided at an end of a handle portion, the guide wire portion being configured to extend through the cannulated openings of the first and second members of the device, and the first drive projection being configured to mate with the first drive aperture of the first head member of the first member. The system further comprises a second instrument comprising a handle portion, a second drive projection provided at an end of the handle portion, and an opening extending into the second drive projection configured to accept the guide wire portion of the first instrument therein, the second drive projection being configured to mate with the second drive aperture of the second head member of the second member. The system also comprises a sizing instrument comprising a through hole extending from a tip of the sizing instrument, a groove aligned with the through hole and a plurality of sizing markings proximate to the groove that correspond to differently sized second members of the device, the through hole and the groove being configured to accept the guide wire portion of the first instrument therein.

In another aspect, the present disclosure provides instruments and related methods of use for installing a soft tissue (e.g., tendon or ligament) retention device during a soft tissue-to-bone attachment procedure. The instrument allows multiple functions to be performed through single hand manipulation thereof. The installation instrument provides for implant gauging, implant insertion, implant compression and/or implant fixation during the attachment procedure.

In some embodiments, the installation instrument comprises a handle portion configured to allow a user to hold and manipulate the installation instrument with one hand (e.g., via extending a digit through an aperture thereof, such as a user's thumb). In some embodiments, the installation instrument comprises a gauging portion extending from one side of the handle portion configured to aid in determining (e.g., gauging) an appropriate size (e.g., length) of a soft tissue retention implant to utilize with a particular bone. In some embodiments, the installation instrument comprises an insertion and fixation portion extending from a side of the handle portion configured to selectively/temporarily engage at least a portion of the soft tissue retention implant during the insertion and attachment procedure. In some embodiments, the installation instrument allows one-handed fixation and compression of the soft tissue retention implant.

In some embodiments, the handle portion comprises a ring (i.e., annulus) sized for reception onto a thumb of the user's hand, the gauging portion comprises a rod extending radially from a boss on an outer surface area of the ring, and the insertion and fixation portion comprises a head extending radially from another outer surface area of the ring with a tip configured to selectively/temporarily engage the soft-tissue retention implant for insertion and fixation of the retention implant. In one embodiment, the tip is threaded. In some embodiments, the gauging portion is sized to receive a gauge with visual indications/demarcations in order to delineate an appropriate size of the soft tissue retention implant for the particular bone. In one embodiment, the gauging portion is situated 180 degrees from the insertion and fixation portion on the handle portion, thereby forming a double-ended instrument.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure. The drawings may or may not be drawn to scale. Illustrative dimensions and aspects are provided in some of the figures, which may be altered as appropriate.

DETAILED DESCRIPTION FOR CARRYING OUT THE INVENTION

Figure 1:
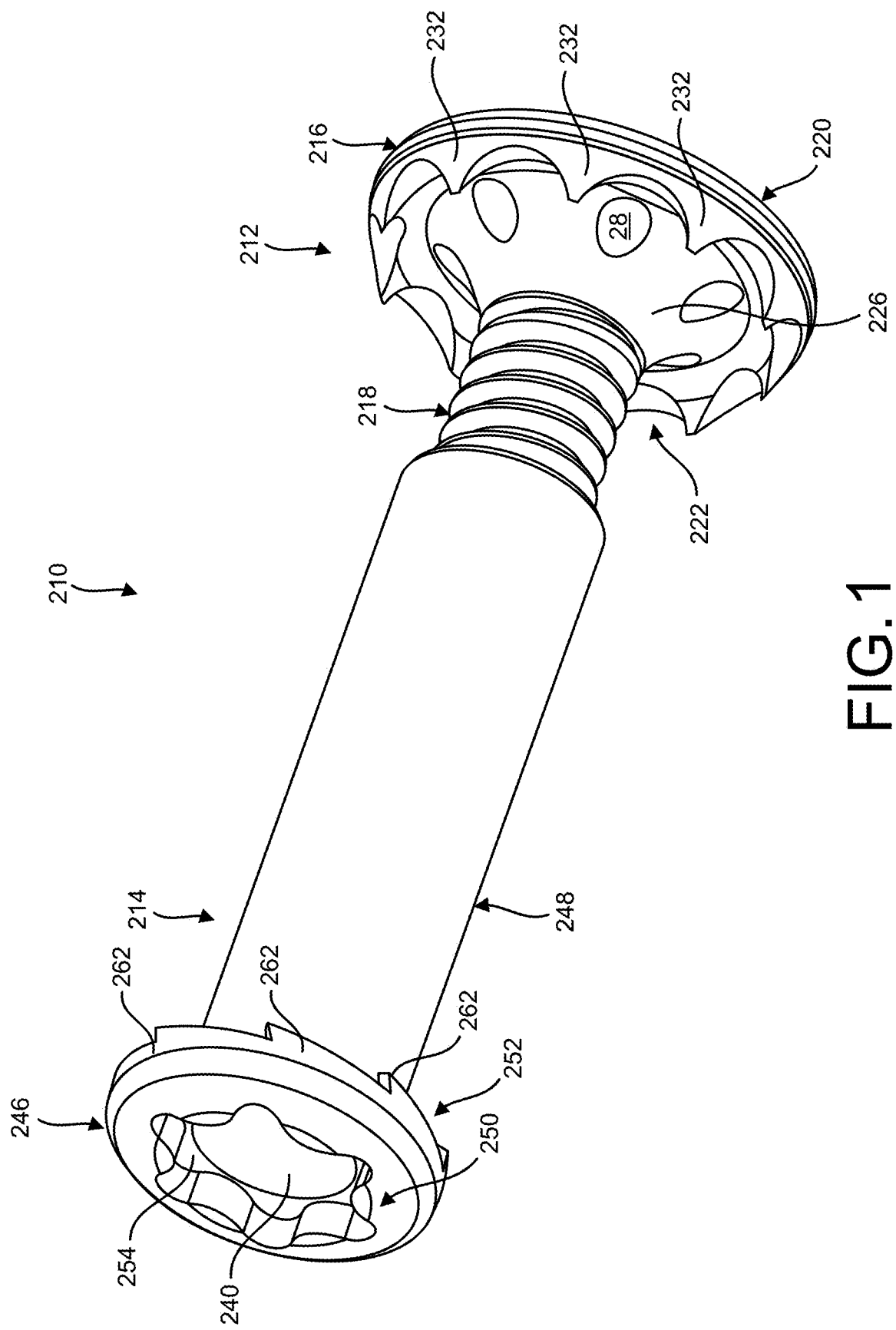
FIG. 1 illustrates a perspective view of an exemplary embodiment of a soft tissue and bone retention device or implant, in an assembled configuration, comprising a soft tissue tack member and a bone anchor member, in accordance with an aspect of the present disclosure.
Figure 2:
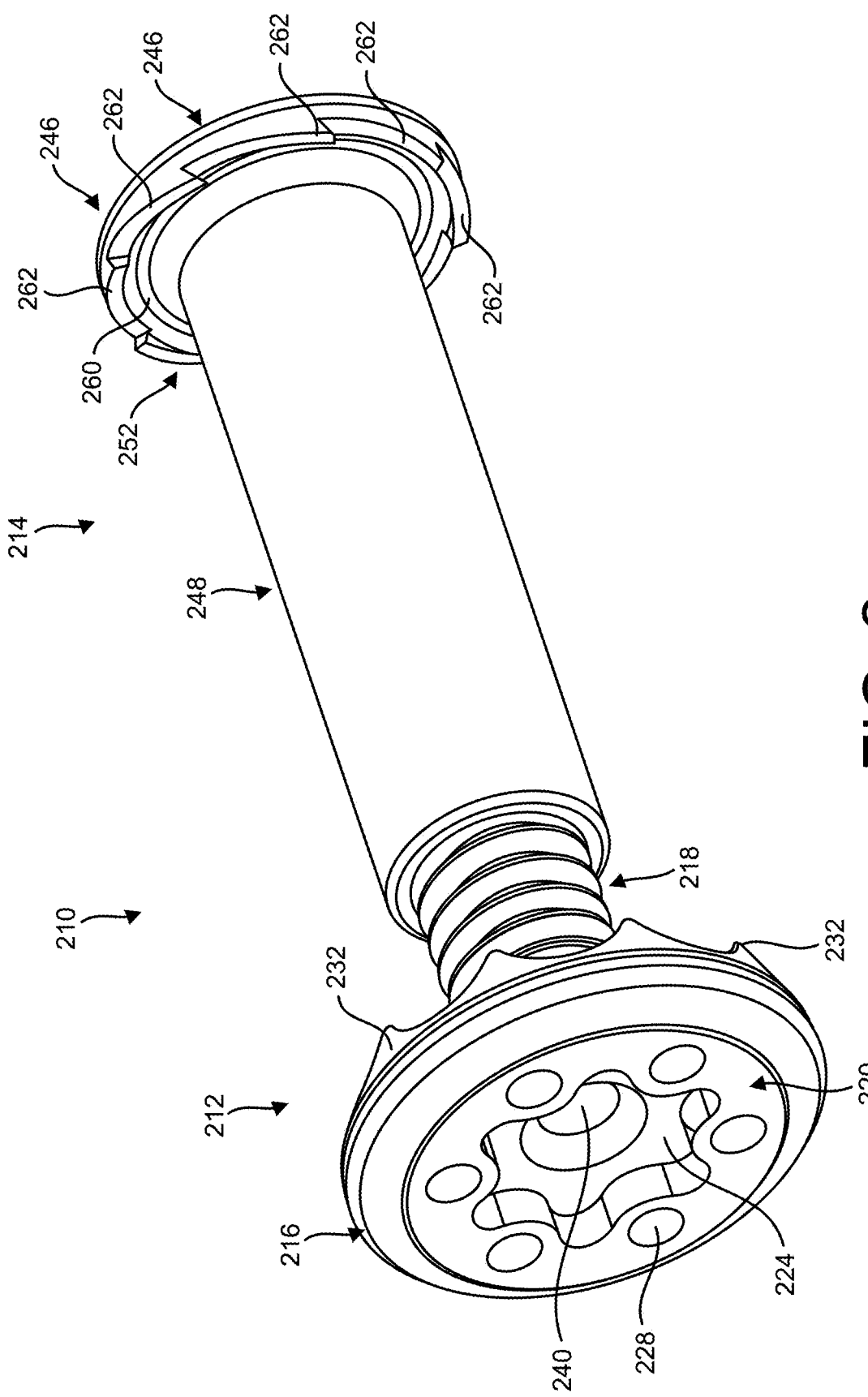
FIG. 2 illustrates another perspective view of the soft tissue and bone retention device of FIG. 1.
Figure 3:
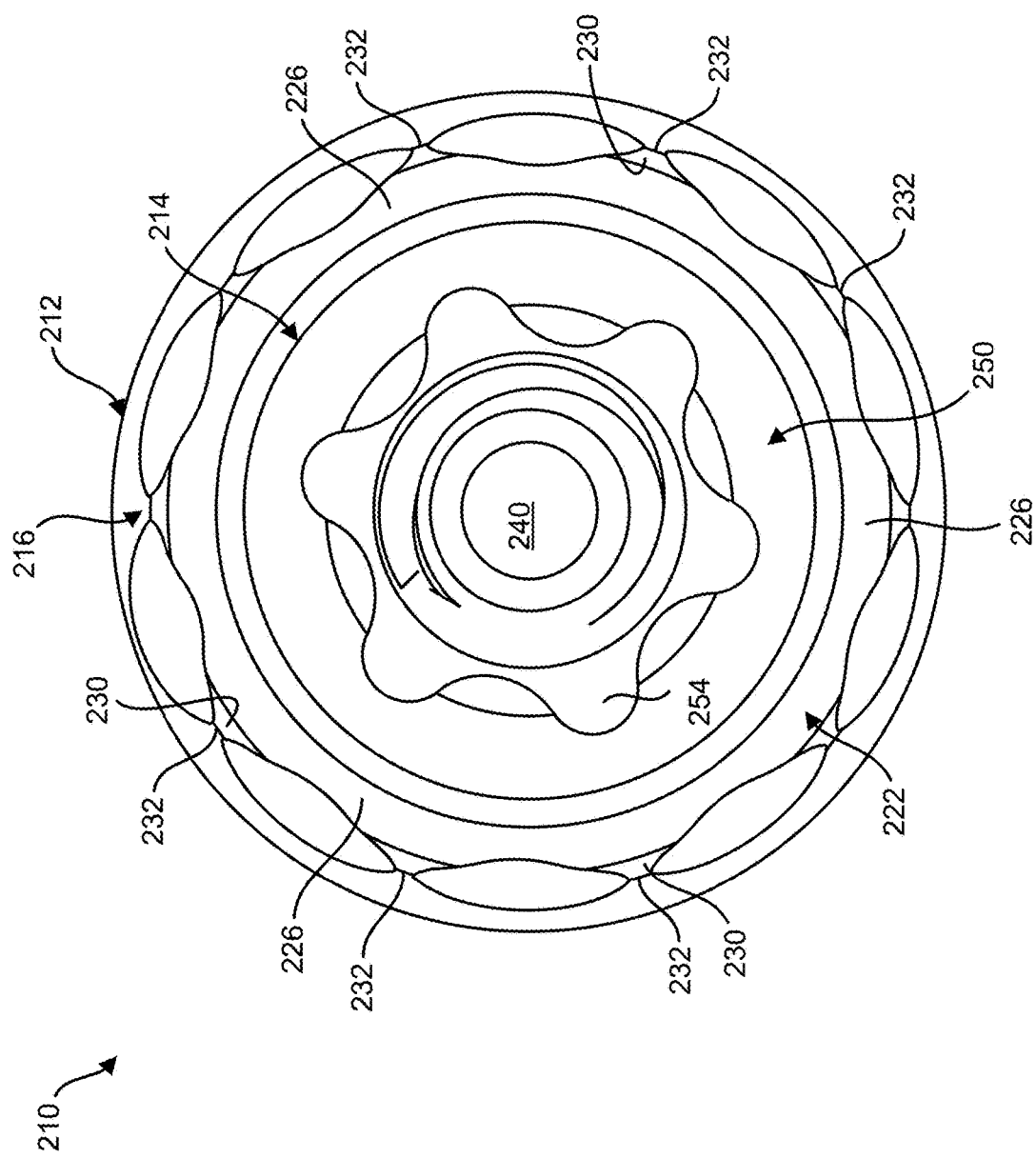
FIG. 3 illustrates a bottom view of the soft tissue and bone retention device of FIG. 1.
Figure 4:
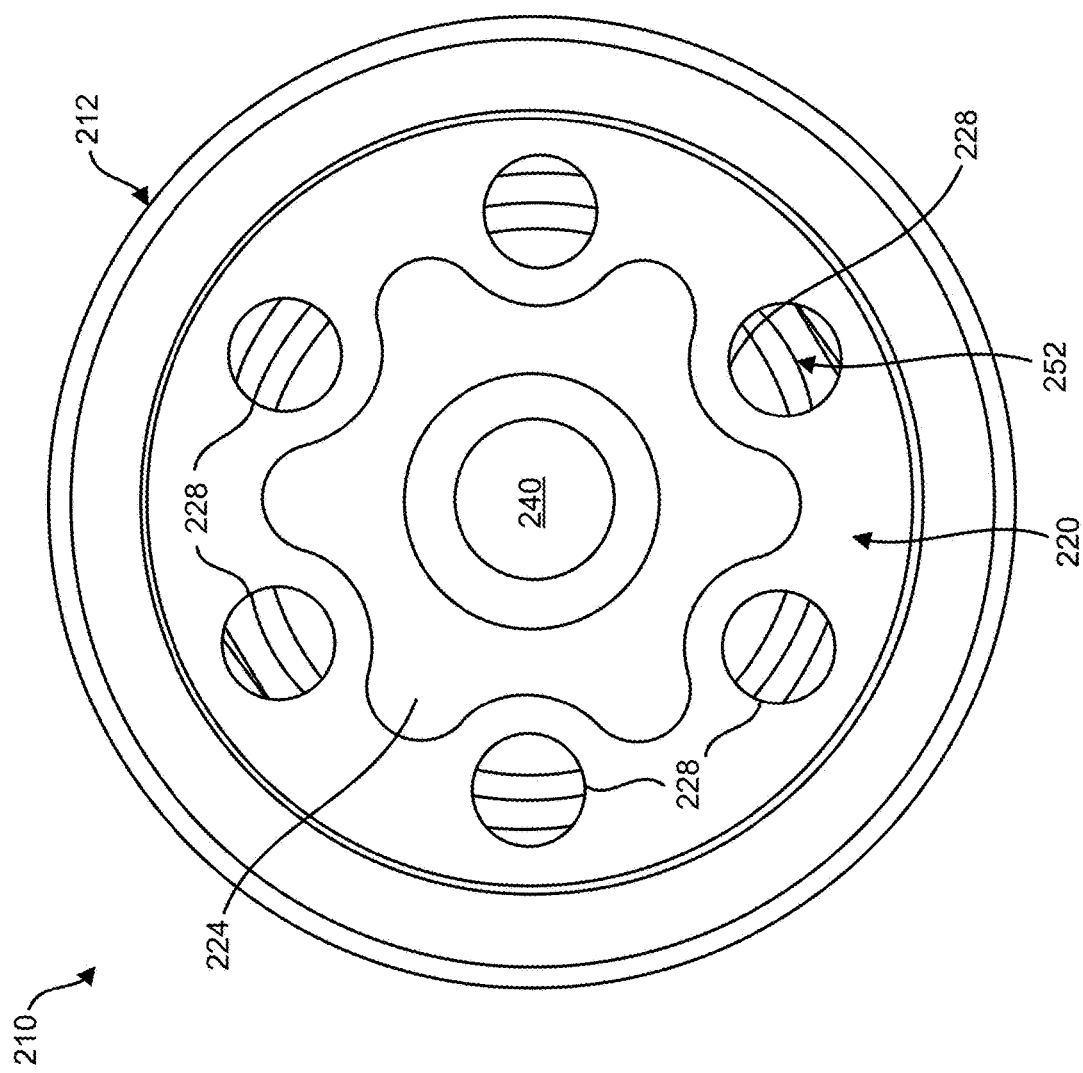
FIG. 4 illustrates a top view of the soft tissue and bone retention device of FIG. 1.
Figure 5:
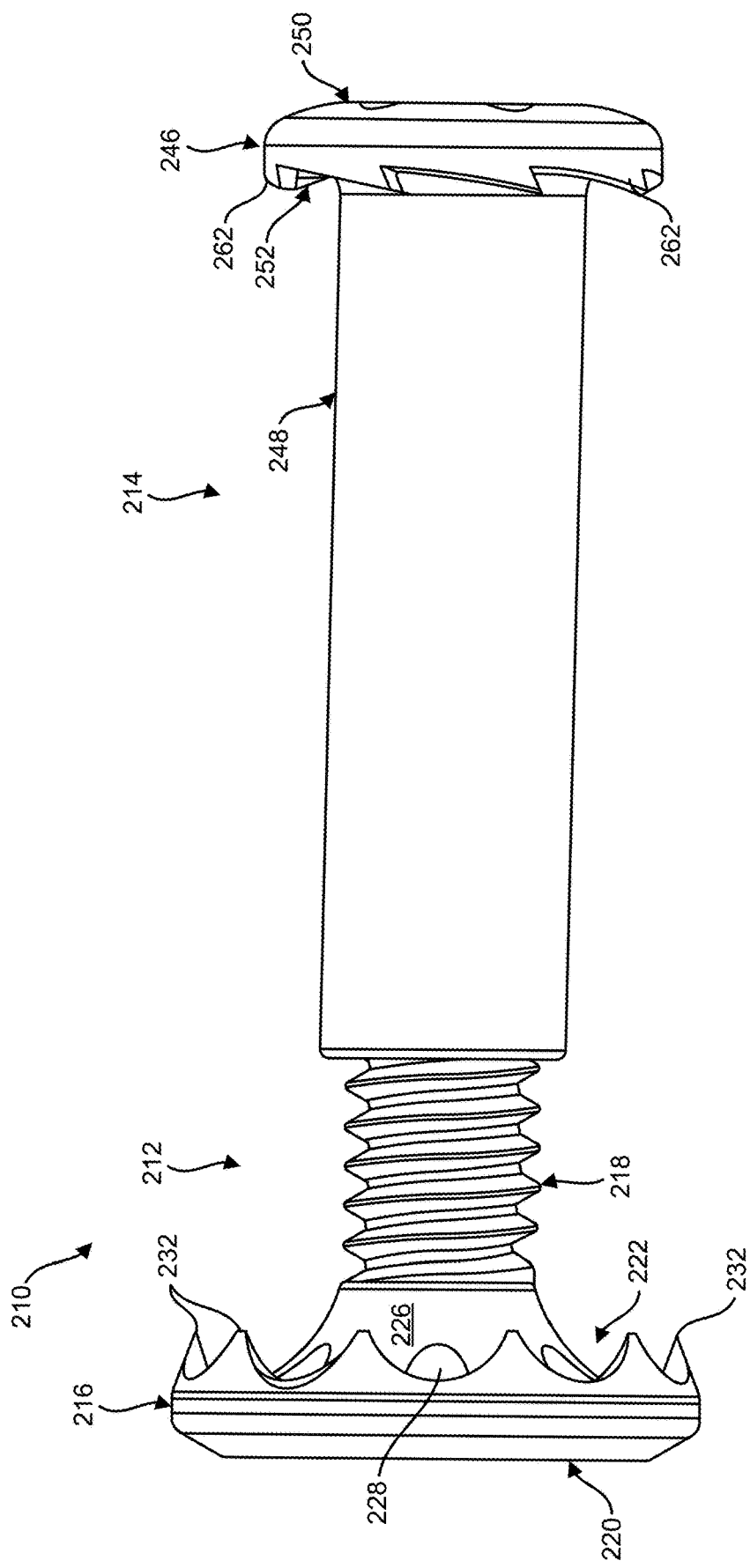
FIG. 5 illustrates a side view of the soft tissue and bone retention device of FIG. 1.
Figure 6:
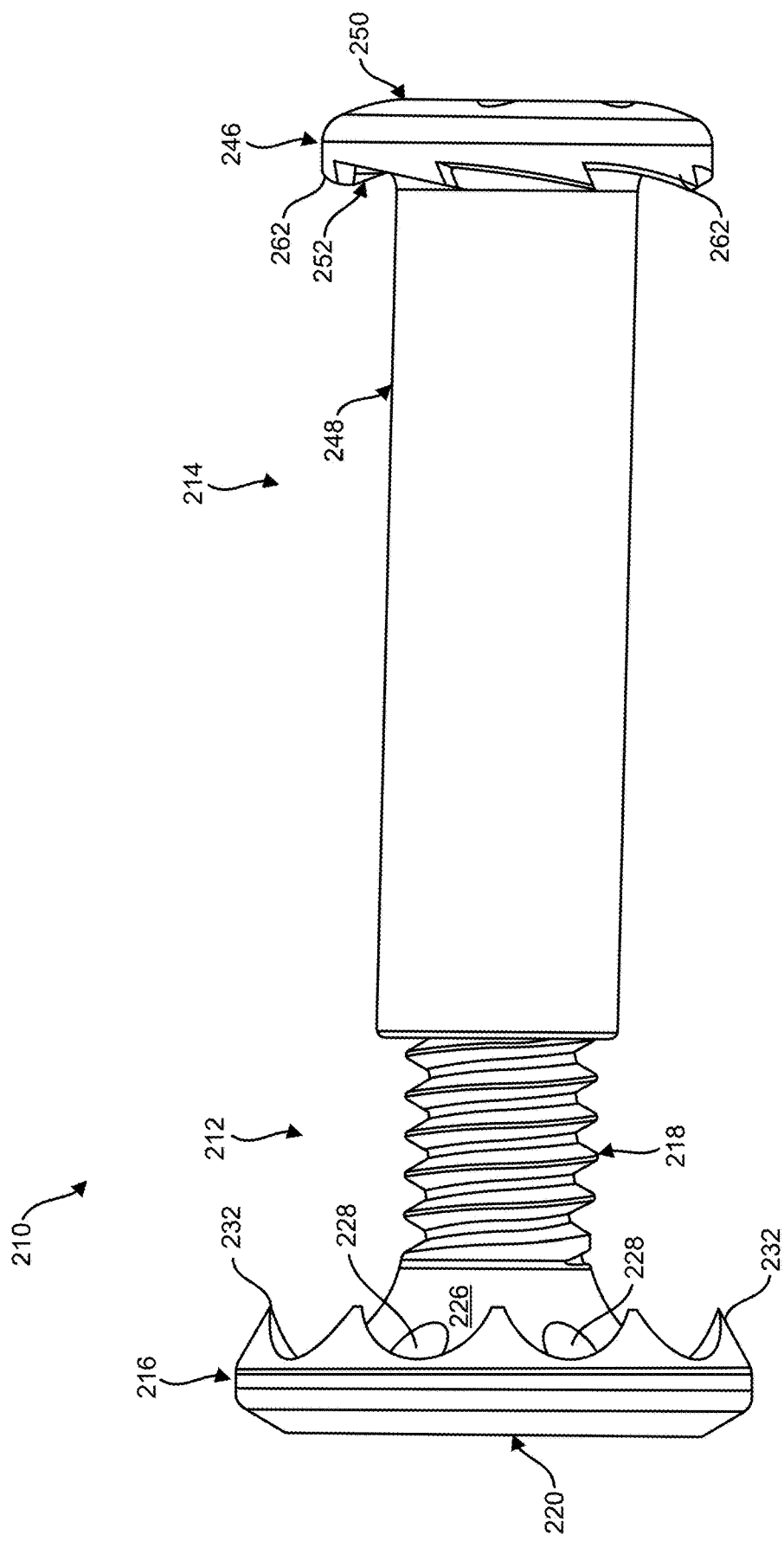
FIG. 6 illustrates another side view of the soft tissue and bone retention device of FIG. 1.
Figure 7:
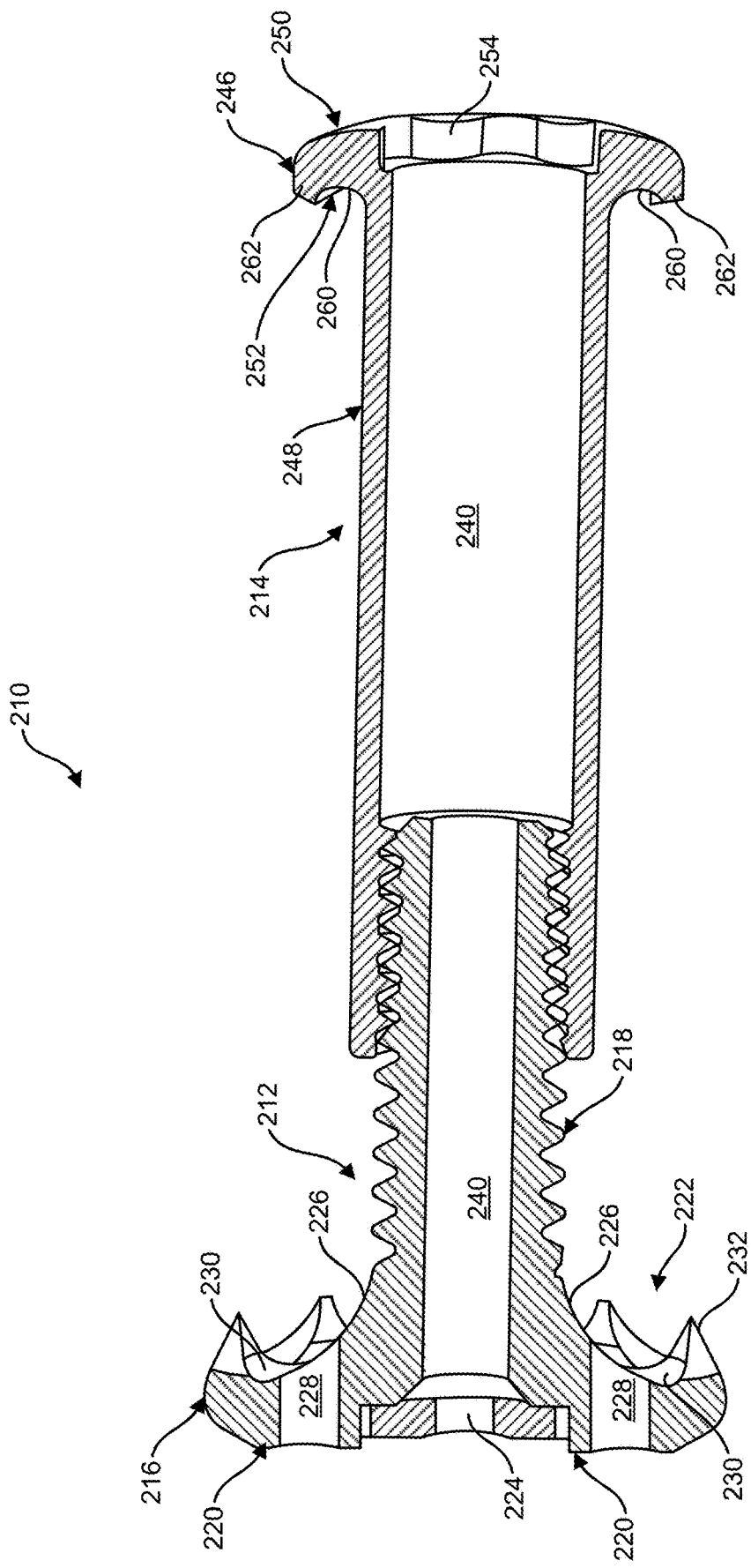
FIG. 7 illustrates a cross-sectional side view of the soft tissue and bone retention device of FIG. 1.
Figure 8:
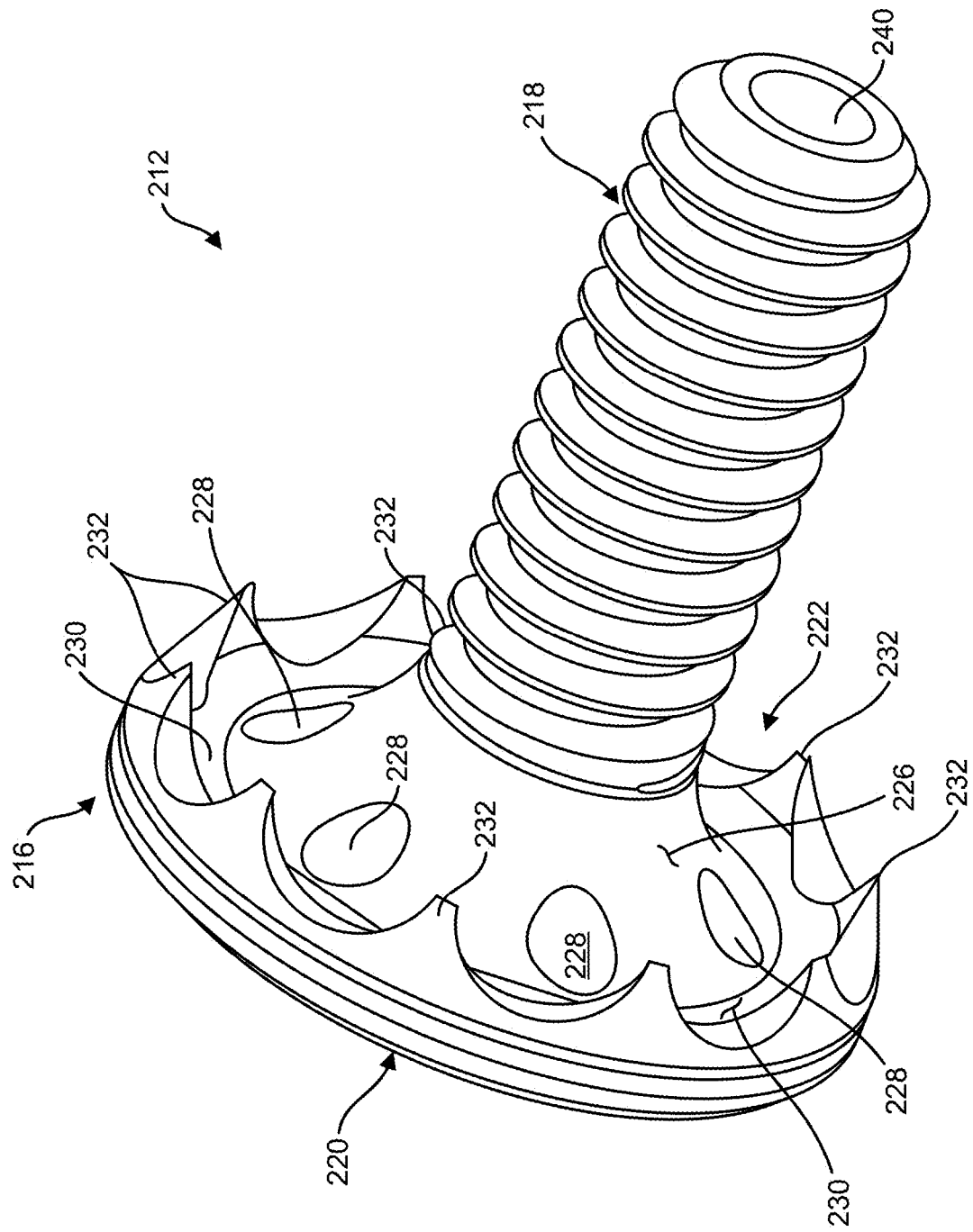
FIG. 8 illustrates a bottom perspective view of a soft tissue tack member of the soft tissue and bone retention device of FIG. 1.
Figure 9:
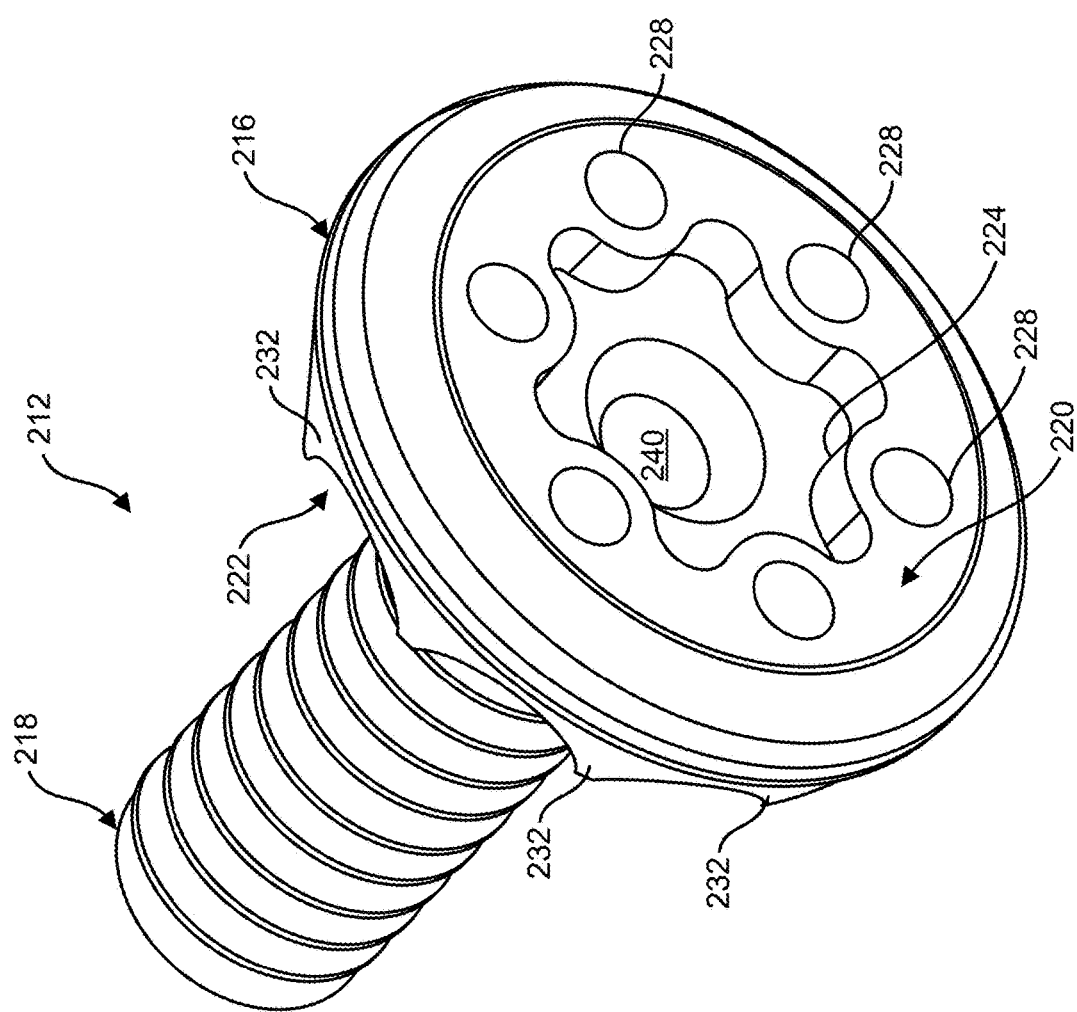
FIG. 9 illustrates an elevational perspective view of the soft tissue tack member of FIG. 8.
Figure 10:
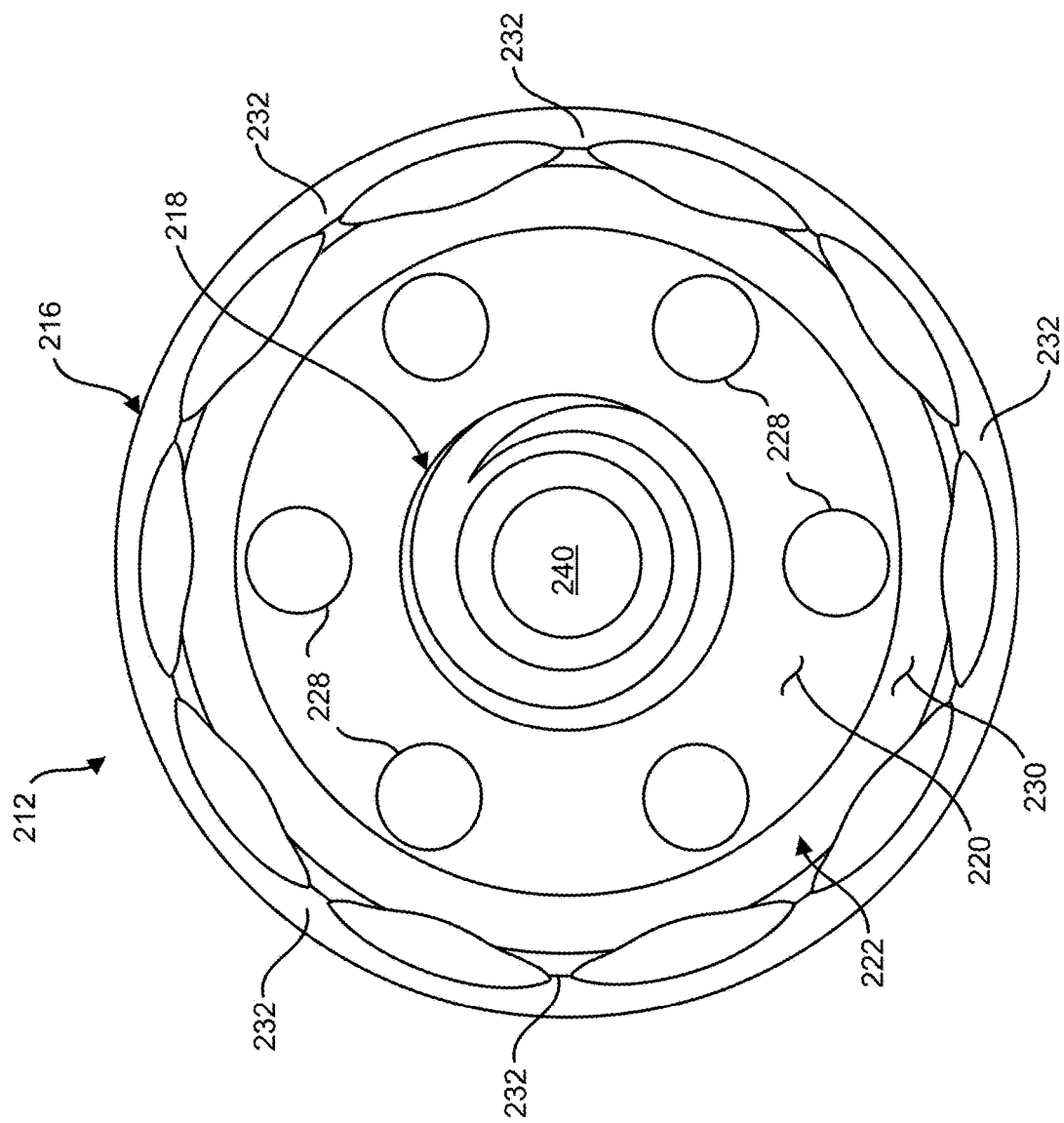
FIG. 10 illustrates a bottom view of the soft tissue tack member of FIG. 8.
Figure 11:
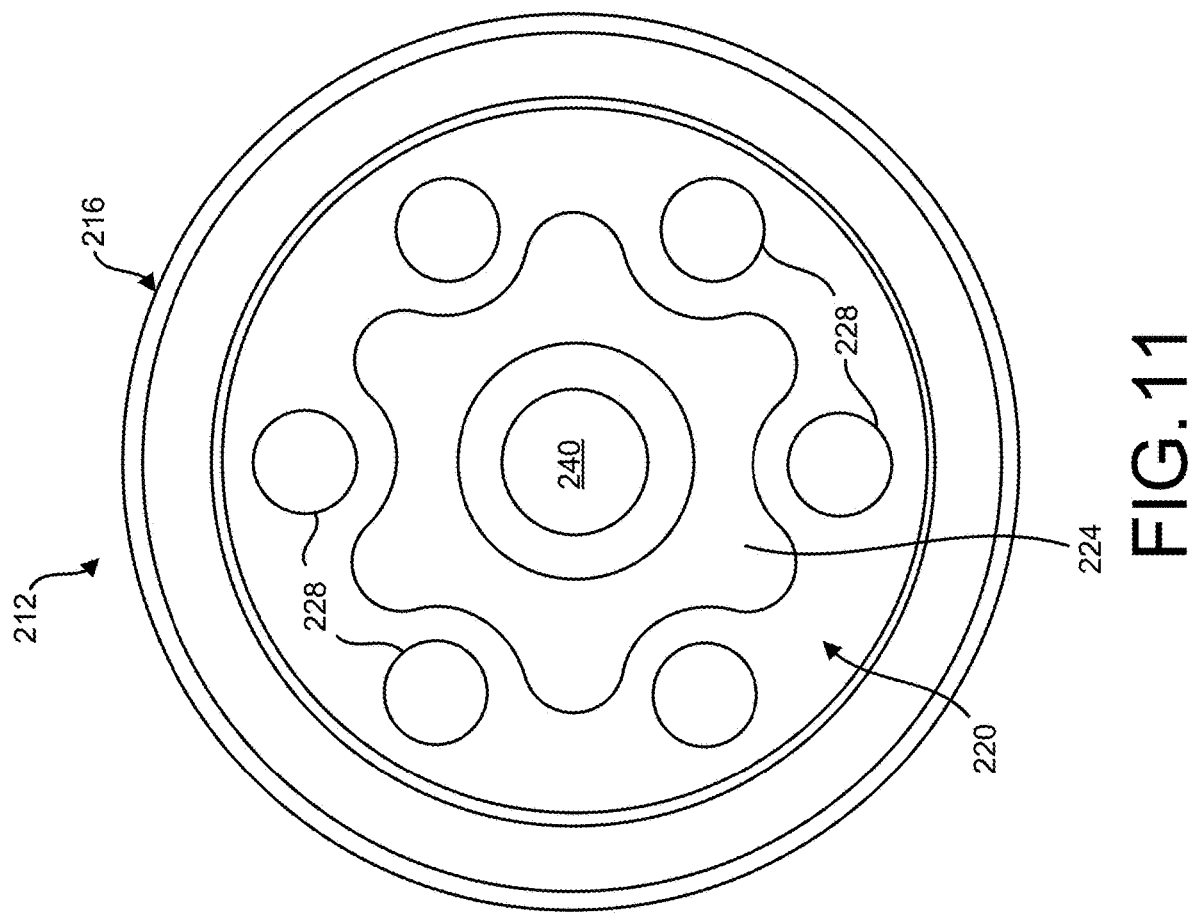
FIG. 11 illustrates a top view of the soft tissue tack member of FIG. 8.
Figure 12:
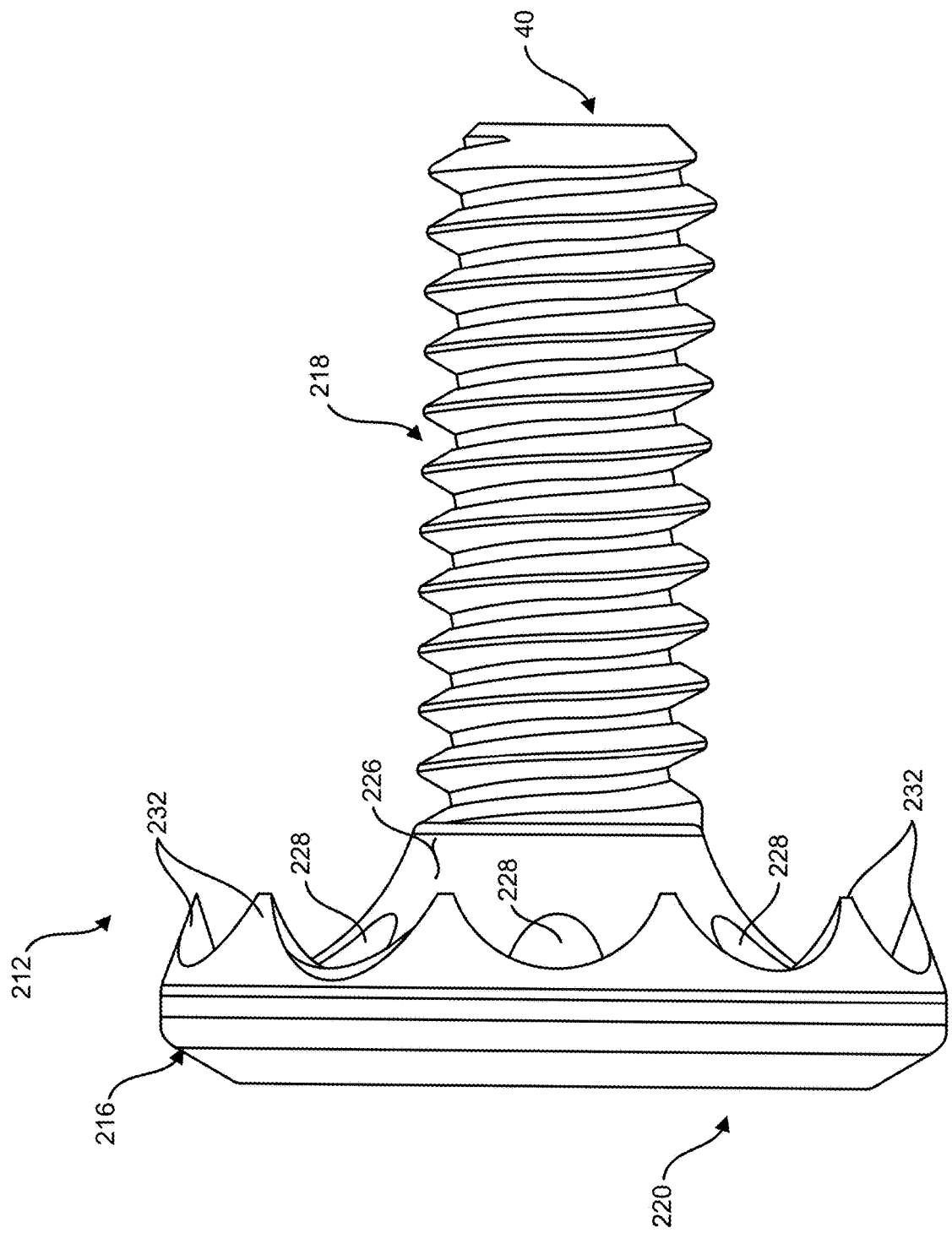
FIG. 12 illustrates a side view of the soft tissue tack member of FIG. 8.

Generally stated, disclosed herein are devices, implants, instrumentation, systems and related methods for retaining or coupling soft tissue to bones. The systems, instruments and related methods may facilitate preparation of a bone to accept the devices, implants, and systems therein/therethrough, implantation/insertion of the devices, implants, and systems into the prepared bone, and/or selection of properly sized devices, implants, and systems for a particular bone.

In this detailed description and the following claims, the words proximal, distal, anterior or plantar, posterior or dorsal, medial, lateral, superior and inferior are defined by their standard usage for indicating a particular part or portion of a bone (or any other anatomical structure) or device/implant/system/instrument according to the relative disposition of the natural bone (or any other anatomical structure) or directional terms of reference. For example, "proximal" means the portion of a device/implant/system/instrument nearest the torso, while "distal" indicates the portion of the device or instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot and/or ankle, the term "dorsal" refers to the top of the foot and the term "plantar" refers the bottom of the foot.

In some embodiments, the soft tissue retention devices, implants, instrumentation, systems and related methods of the present disclosure may comprise, or include one or more component, portion, aspect, function or the like that is similar to, or the same as, that disclosed in International PCT Patent Appl. No. PCT/US2017/048780 (hereinafter the '780 application), filed on Aug. 26, 2017, and entitled Tendon Retention Device, U.S. patent application Ser. No. 15/687,450 (hereinafter the '450 application), filed on Aug. 26, 2017, entitled Tendon Retention Device, U.S. Provisional Patent Appl. No. 62/379,789 (hereinafter the '789 application), filed on Aug. 26, 2016, U.S. Provisional Patent Appl. No. 62/454,100 (hereinafter the '100 application), filed on Aug. Feb. 3, 2017, and/or U.S. Provisional Patent Appl. No. 62/500,574 (hereinafter the '574 application), filed on May 3, 2017, which are hereby expressly incorporated herein by reference in their entireties. In some embodiments, the soft tissue retention device instrumentation, systems and related methods of the present disclosure may be utilized to implant a soft tissue retention device of the '780 application, the '450 application, the '789 application, the '100 application and/or the '574 application to attach or fix soft tissue to a bone.

Approximating language, as used herein throughout disclosure, may be applied to modify any quantitative representation that could permissibly vary without resulting in a change in the basic function to which it is related. Accordingly, a value modified by a term or terms, such as "about" or "substantially," is not limited to the precise value specified. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. In some instances, the approximating language may correspond to the precision of an instrument for measuring the value.

Referring to the drawings, wherein like reference numerals are used to indicate like or analogous components throughout the several views, and with particular reference to FIGS. 1-7, there is illustrated an exemplary embodiment of a soft tissue (such as, but not limited to, tendon or ligament) retention, coupling, fixation or securement device, implant or system 10 configured to couple, retain, fix, and/or secure soft tissue to an associated or desired bone (such as, but not limited to, a relatively small bone (e.g., a bone of the foot or hand)). In some embodiments, the soft tissue retention device 10 may be particularly configured and/or advantageous for retention of a flexor digitorum longus tendon and an associated bone, such as, but not limited to, the plantar aspect of a proximal phalangeal base (bone) particularly, but not necessarily, for the correction of a toe contracture. However, the soft tissue retention device 10 may be configured and/or effectively utilized to retain, couple or fix any soft tissue (e.g., a tendon, ligament or the like) to any bone (e.g., any relatively small bone, such as a phalange, metatarsal or metacarpal bone) of a patient (e.g., a human patient).

The soft tissue retention device 10 is preferably, but not necessarily, made of a biocompatible metal such as titanium, stainless steel, an alloy, or the like, or other biocompatible material such as plastic, ceramic or the like.

The soft tissue retention device (or system or implant) 10 may comprise a first component 12 and a second component 14, the nomenclature first and second being arbitrary. The first component 12, without being restrictive, may be configured as a soft tissue tack member, portion or component, while the second component 14, without being restrictive, may be may be configured as bone anchor member, portion or component 12. When implanted, the soft tissue tack member 12 and the bone anchor member 14 are configured to nest and removably or fixedly couple together. As explained further below, one of the soft tissue tack member 12 and the bone anchor member 14 may be configured as an externally threaded male portion, and the other of the soft tissue tack member 12 and the bone anchor member 14 may be configured as an internally threaded female portion (for threadably mating with the externally threaded male portion).

In some embodiments, the soft tissue retention device 10 may be a two-piece device comprised of only the soft tissue tack member 12 and the bone anchor member 14. In some other embodiments, the soft tissue retention device 10 may comprise additional components over the soft tissue tack member 12 and the bone anchor member 14. In some embodiments, the soft tissue tack member 12 may be a one-piece or integral (e.g., monolithic) component. In some other embodiments, the soft tissue tack member 12 may be comprised of two or more separate and distinct components. In some embodiments, the bone anchor member 14 may be a one-piece or integral (e.g., monolithic) component. In some other embodiments, the bone anchor member 14 may be comprised of two or more separate and distinct components.

As shown in FIGS. 1-13, the soft tissue tack member 12 incudes a head or base portion 16 and a threaded shaft portion 18 extending from the head portion 16. The shaft portion 18 may be externally threaded (i.e., configured as a male portion or component) as shown in FIGS. 1-13, or alternatively the shaft portion 18 may be internally threaded (i.e., configured as a female portion or component) (not shown). The head portion 16 may be generally disc-shaped (i.e., substantially flat, thin and curricular shaped) (although other shapes may be used). As also shown in FIGS. 1-13, the head portion 16 may have a generally planar outer or upper side, face or surface 20 and an inner or under side, face or surface 22. The shaft portion 18 extends from a central or center portion of the inner side 22 of the head portion 16. The shaft portion 18 may extend generally transverse from the inner side 22 of the head portion 16. The shaft portion 18 may define a first diameter, and the head portion 16 may define a second diameter that is larger than the first diameter.

As shown in FIGS. 2, 4, 7, 9, 11 and 13, the head portion 16 includes a drive or torque aperture, indentation, cavity or slot 24 in the outer side 20 thereof that is configured to mate with an instrument, tool or guide member for rotating (or preventing rotation), inserting or aiding in the insertion, guiding, installation or implantation of the soft tissue tack member 12 into/through soft tissue and a bone, as explained further below. The drive aperture 24 is of a non-circular cross-sectional shape so that that a torque device can mate therein and an apply a rotational force to the soft tissue tack member 12.

As shown in FIGS. 2-4, 7-11 and 13, the head portion 16 and the shaft portion 18 may include a cannulated opening 40 extending therethrough about an axis (e.g., a longitudinal axis and/or an axis of rotation) of the tack member 12. The tack member 12, as a whole, may thereby be cannulated. The drive aperture 24 may be aligned with, or formed as part as, the outer portion of the cannulated opening 40 of the tack member 12. If the shaft portion 18 is internally threaded as opposed to being externally threaded as shown in FIGS. 1-13, the cannulated opening 40 thereof may include the internal threads.

As shown in FIGS. 1, 3, 5-8, 10, 12 and 13, the inner side 22 of the head portion 16 may include an annular sloped (e.g., arcuately concave) or angled transition surface portion 26 that extends or transitions to/from the threaded shaft portion 18. As shown in FIGS. 1, 2 and 4-13, the head portion 16 may include a plurality of through holes 28 extending therethrough that are circumferentially spaced about the periphery or outer sides of the drive aperture 24 and shaft portion 18. The through holes 28 may extend from the (planar) outer side surface 20 of the head portion 16 to the outer peripheral portion of the transition portion 26 of the inner side 22 of the head portion 16. The through holes 28 are configured to allow soft tissue to extend therein/therethrough when the soft tissue retention device 10 is tightened/compressed onto the soft tissue and adjacent bone to exsanguinate and securely grip/couple the soft tissue.

Figure 13:
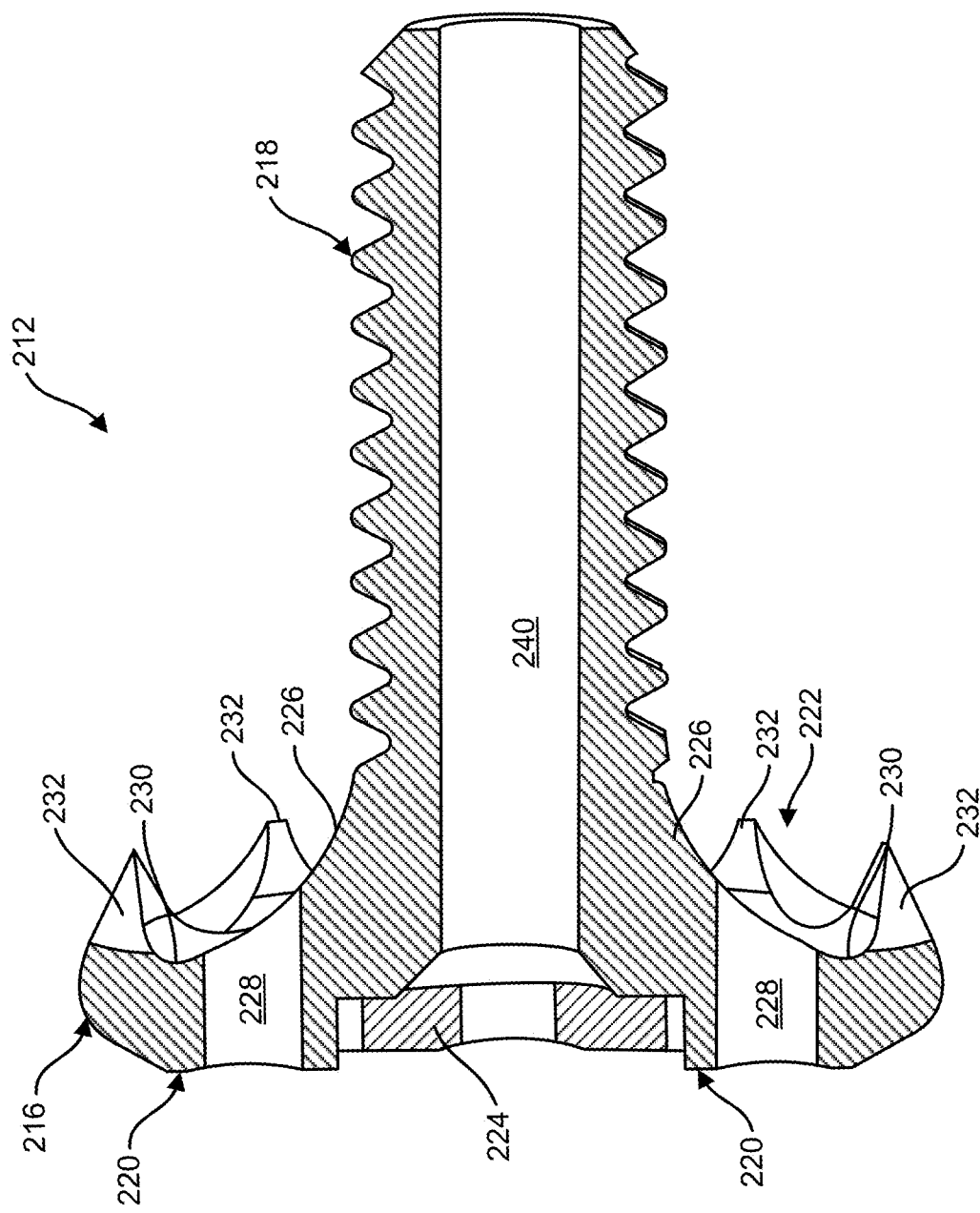
FIG. 13 illustrates a cross-sectional side view of the soft tissue tack member of FIG. 8.
Figure 14:
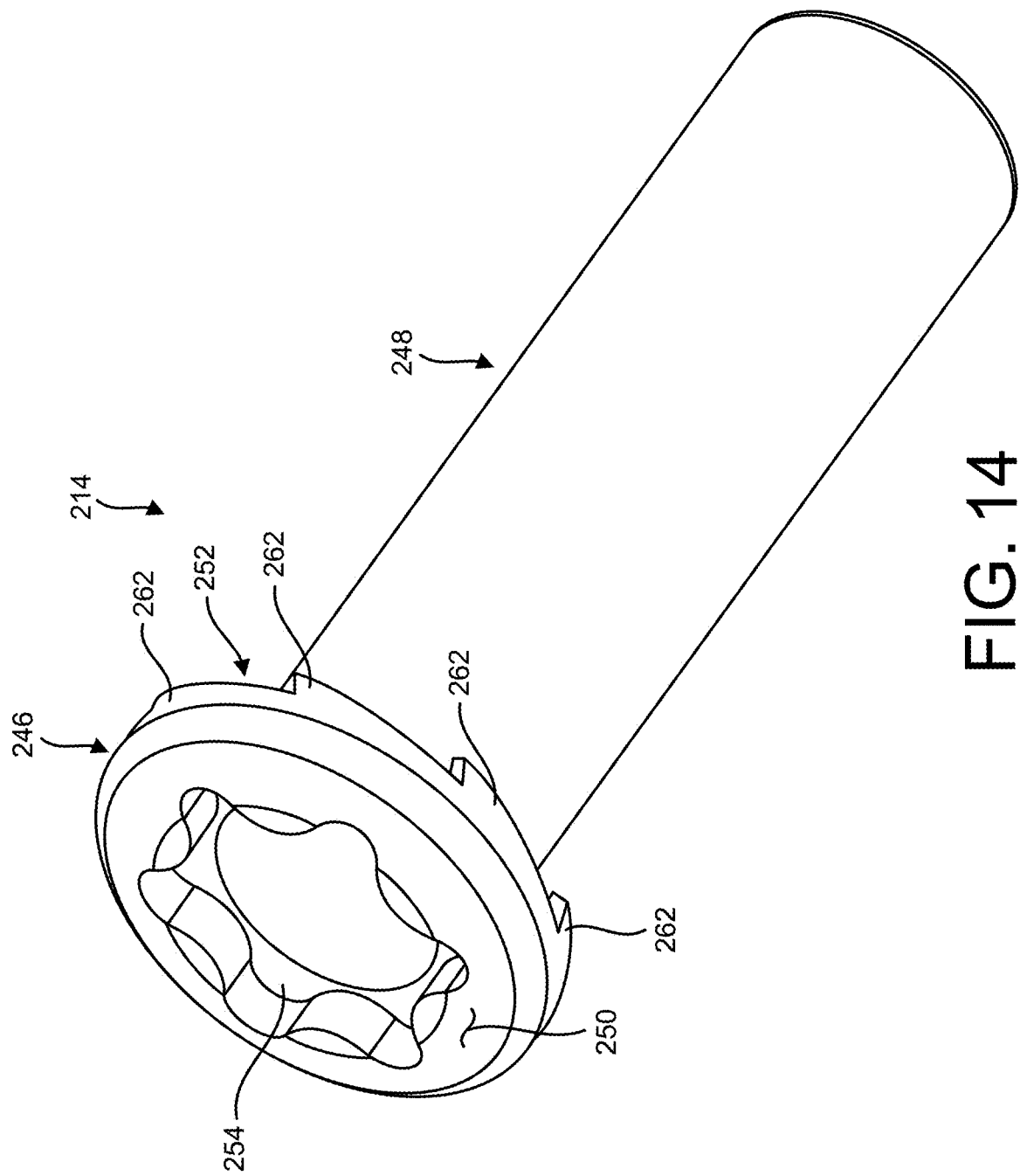
FIG. 14 illustrates a bottom perspective view of a bone anchor member of the soft tissue and bone retention device of FIG. 1.
Figure 15:
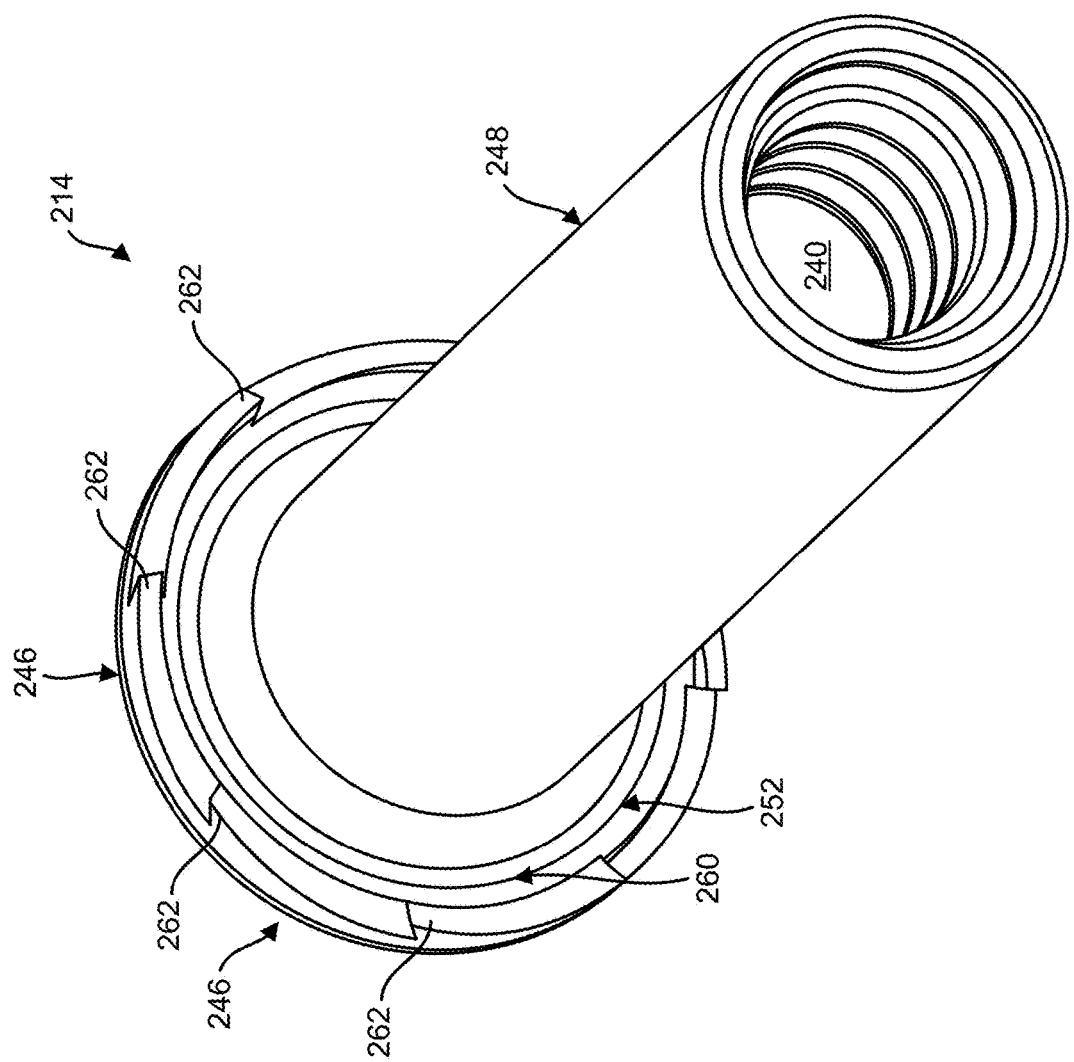
FIG. 15 illustrates a top perspective view of the bone anchor member of FIG. 14.
Figure 16:
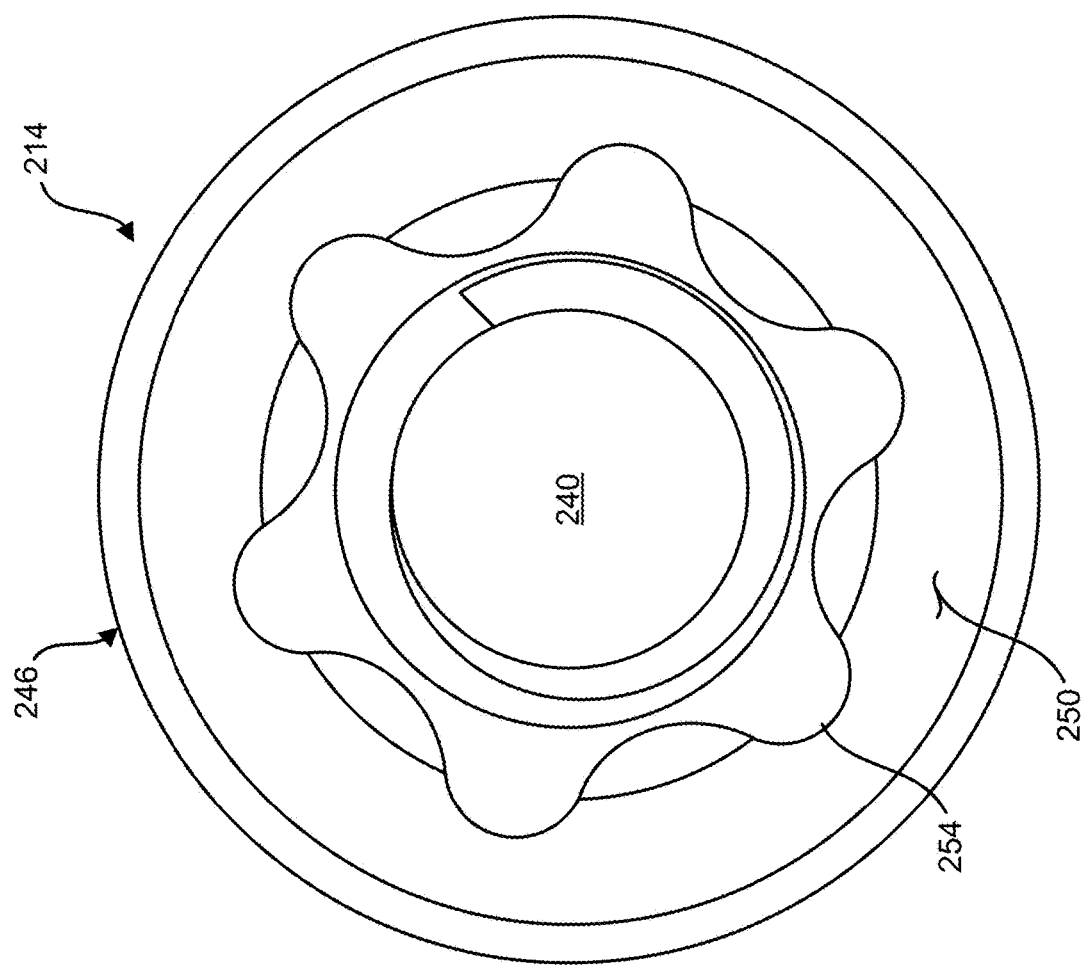
FIG. 16 illustrates a bottom view of the bone anchor of FIG. 14.
Figure 17:
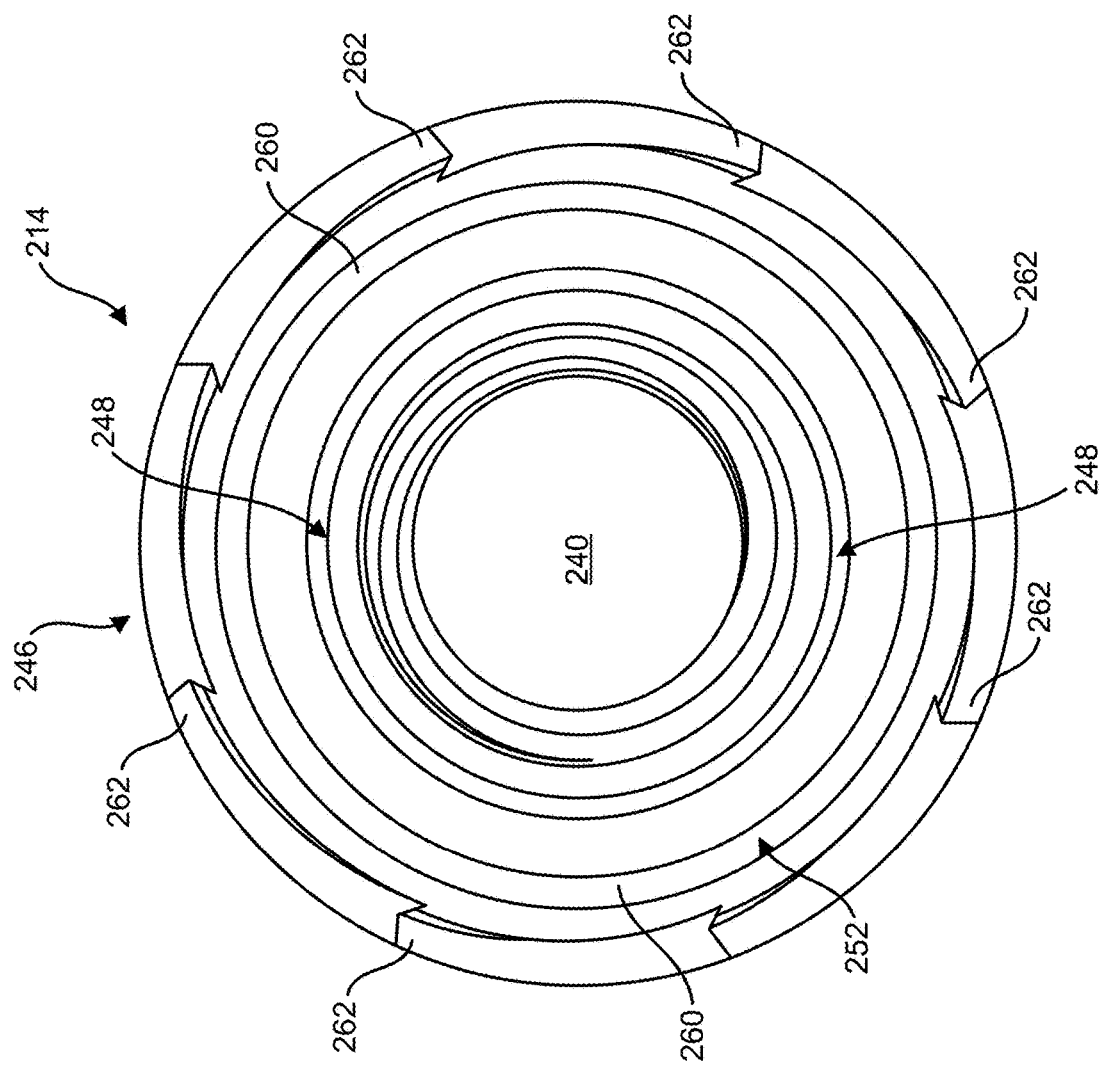
FIG. 17 illustrates a top view of the bone anchor member of FIG. 14.
Figure 18:
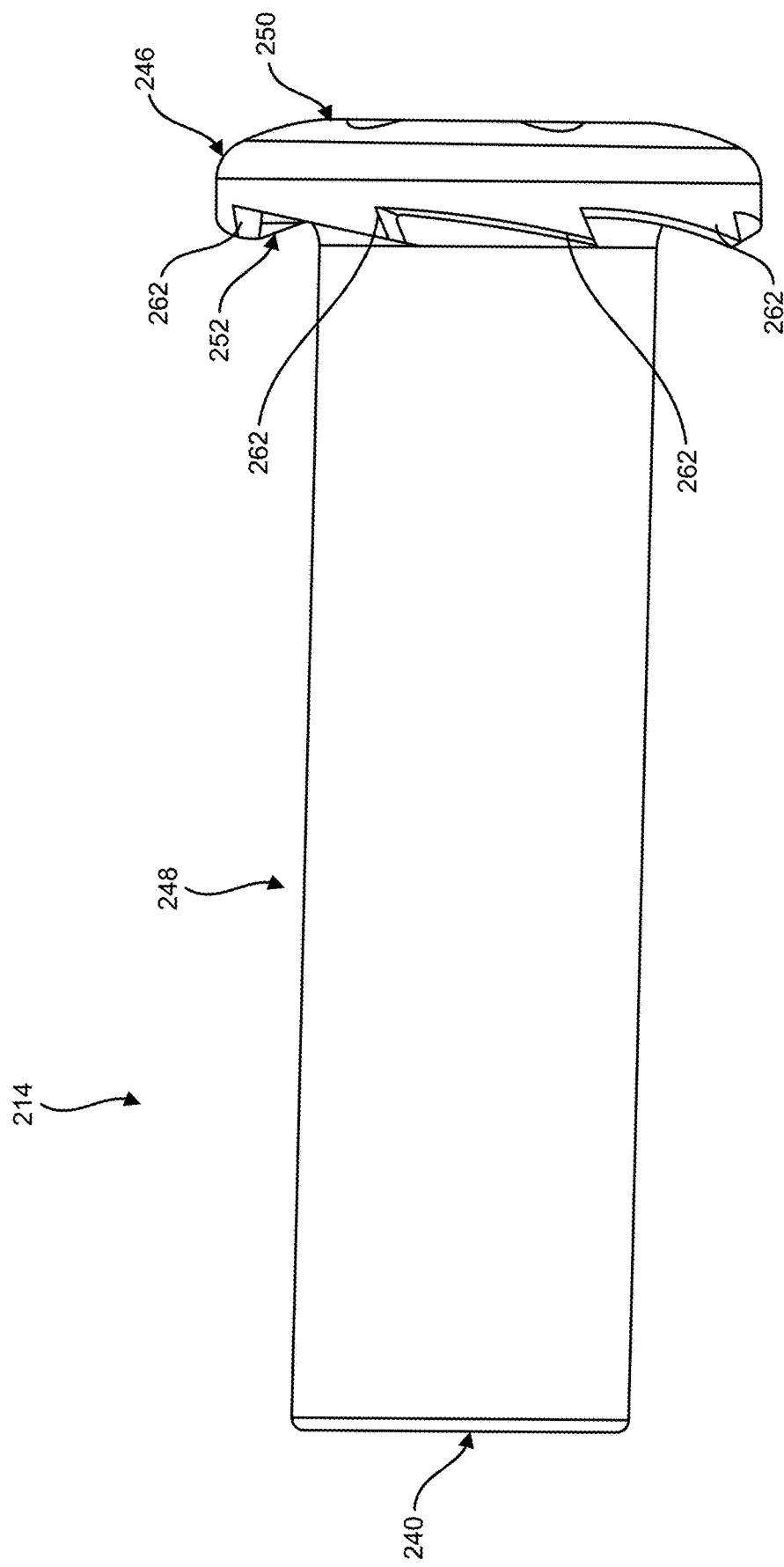
FIG. 18 illustrates a side view of the bone anchor member of FIG. 14.
Figure 19:
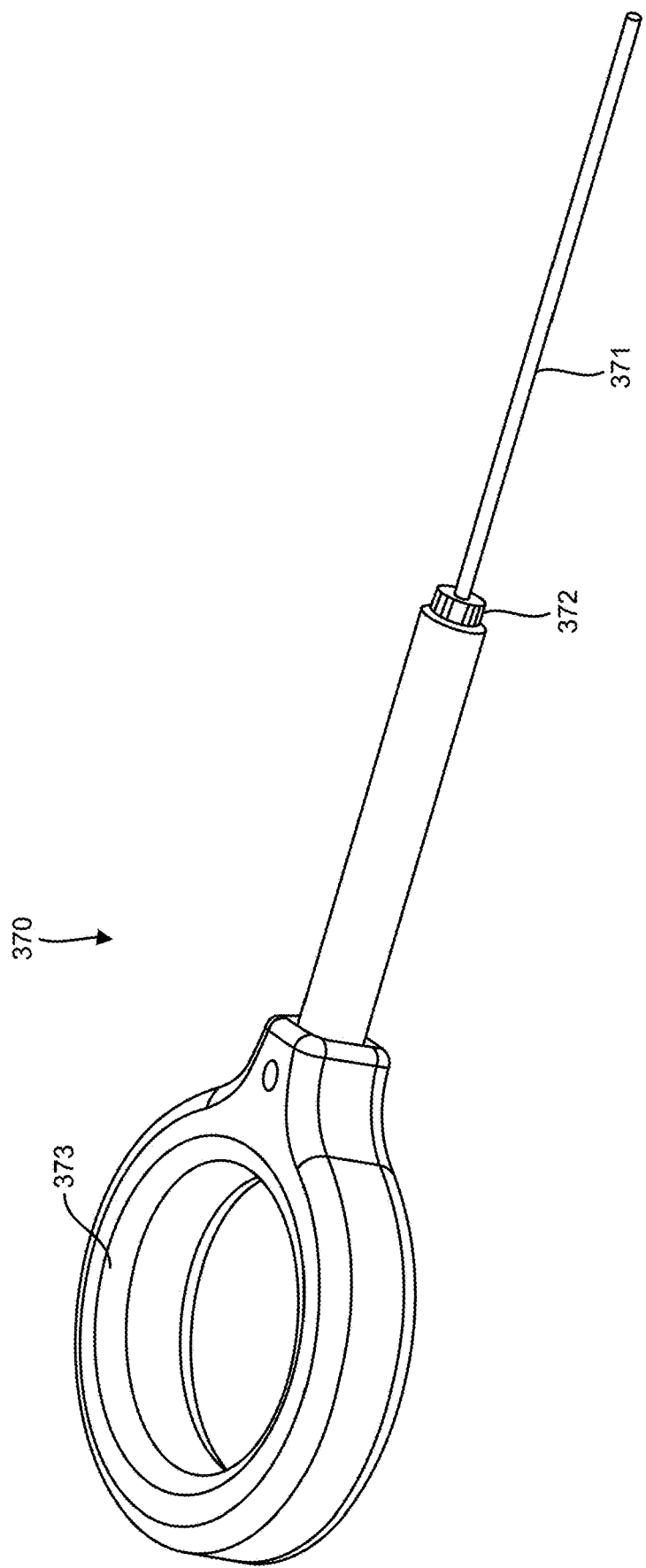
FIG. 19 illustrates a perspective view of an exemplary tack member drive and guide instrument, in accordance with an aspect of the present disclosure.
Figure 20:
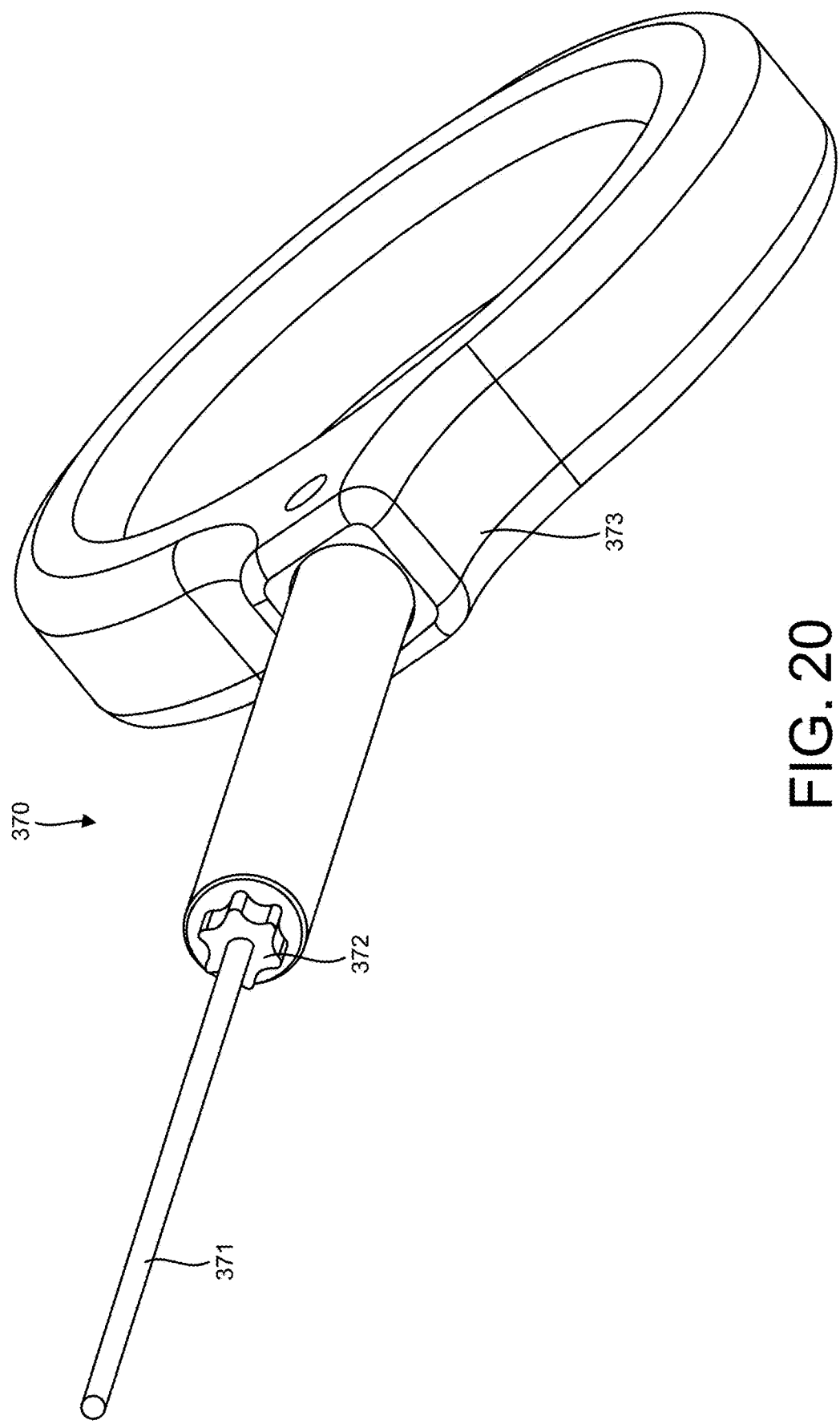
FIG. 20 illustrates another perspective view of the tack member drive and guide instrument of FIG. 19.
Figure 21:
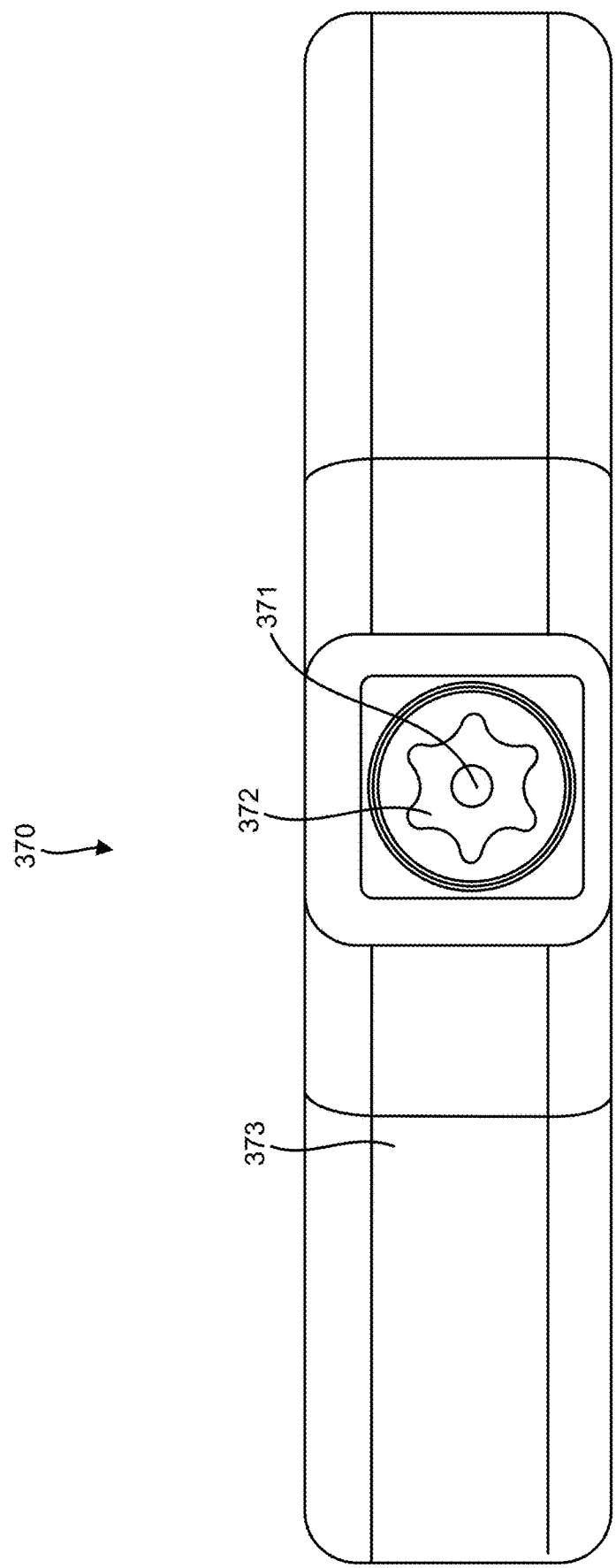
FIG. 21 illustrates a drive end view of the tack member drive and guide instrument of FIG. 19.

As shown in FIG. 13, the inner side 22 of the head portion 16 may also include an annular arcuately concave groove or depression portion 30 that extends between an inner or back side of an outer peripheral row of teeth or projections 32 and the transition portion 28. The annular depression 30 may be configured to contain or filled by the soft tissue when the soft tissue retention device 10 is tightened/compressed onto the soft tissue and adjacent bone. As also shown in FIG. 13, the row of teeth 32 may define the outer periphery of the head portion 16. In some embodiments, the inner side 22 of the head portion 16 may only comprise a single row of the teeth 32 at the periphery thereof. The inner or back side of the teeth 32 may be arcuate (e.g., arcuately concave) and/or planar. The outer side of the teeth 32 may planar and/or arcuate (e.g., arcuately convex or concave). The lateral sides of the teeth 32 (and the gullets extending therebetween) be arcuate (e.g., arcuately concave), and the teeth 32 may narrow as they extend longitudinally away from the inner side 22 of the head portion 16, as shown in FIGS. 1, 2, 5, 6, 8, 9 and 12. In some other embodiments, the lateral sides of the teeth 32 be planar and/or arcuate. The tips of the teeth 32 may be linear/flat or planar. In some other embodiments, the tips of the teeth 32 may be arcuate. The teeth 32 may define an axis that is aligned with the axis of the tack member 12. Stated differently, the teeth 32 may extend along a direction that is aligned or parallel to the axis of the tack member 12 in all directions (and thereby perpendicular or normal to the head portion 16).

As explained above, the threaded shaft portion 18 of the soft tissue tack member 12 is configured to threadably couple with a corresponding or mating threaded shaft portion 48 of the bone anchor member 14, as shown in FIGS. 1-13. As shown in FIGS. 1-7 and 14-18, the bone anchor member 14 includes a head or base portion 46 and the threaded shaft portion 48 extending from the head portion 46. The shaft portion 48 may be internally threaded (i.e., configured as a tubular hollow female portion or component) as shown in FIGS. 1-7 and 14-18, or alternatively the shaft portion 48 may be externally threaded (i.e., configured as a male portion or component) (not shown).

The head portion 46 may be generally disc-shaped (i.e., substantially flat, thin and curricular shaped) (although other shapes may be used). As also shown in FIGS. 1-7 and 14-18, the head portion 46 may have a generally planar outer or upper side, face or surface 50 and an inner or under side, face or surface 52. The shaft portion 48 extends from a central or center portion of the inner side 52 of the head portion 46. The shaft portion 48 may extend generally transverse from the inner side 52 of the head portion 46. The shaft portion 48 may define a first diameter, and the head portion 46 may define a second diameter that is larger than the first diameter.

As shown in FIGS. 1, 3, 7, 14 and 16, the head portion 46 of the bone anchor member 14 includes a drive or torque aperture, indentation, cavity or slot 54 in the outer side 50 thereof that is configured to mate with an instrument, tool or guide member for rotating (or preventing rotation), inserting or aiding in the insertion, guiding, installation or implantation of the bone anchor member 14 into/through a bone, as explained further below. The drive aperture 54 is of a non-circular cross-sectional shape so that that a torque device can mate therein and an apply a rotational force to the bone anchor member 14.

As shown in FIGS. 1, 3, 7 and 14-17, the head portion 46 and the shaft portion 48 may include a cannulated opening 40 extending therethrough about an axis (e.g., a longitudinal axis and/or an axis of rotation) of the bone anchor member 14. The bone anchor member 14, as a whole, may thereby be cannulated. The drive aperture 54 may be aligned with, or formed as part as, the outer portion of the cannulated opening 40 of the bone anchor member 14. If the shaft portion 48 is externally threaded as opposed to being internally threaded as shown in FIGS. 1-7 and 14-18, the cannulated opening 40 may be void of the threads.

As shown in FIGS. 2, 7, 15 and 17, the inner side 52 of the head portion 46 may include an annular sloped (e.g., arcuately concave) or angled transition surface portion that extends or transitions to/from the threaded shaft portion 48. As also shown in FIGS. 2, 7, 15 and 17, the inner side 52 of the head portion 46 may also include an annular groove or depression portion 60 that extends between an inner or back side of an outer peripheral row of teeth or projections 62 and the transition portion. The annular depression 60 may include an annular planar or flat bottom surface, and arcuately concave side portions formed by the transition surface portion and the inner sides of peripheral teeth 62. The annular depression 60 may be configured to contain or be filled by bone material when the retention device 10 is tightened/compressed onto the adjacent bone.

As shown in FIGS. 1, 2, 5-7, 14, 15, 17 and 18, the peripheral row of teeth 62 may define the circular outer periphery of the head portion 46. In some embodiments, the inner side 52 of the head portion 46 may only comprise a single row of the teeth 62 at the periphery thereof. The inner or back side of the teeth 62 may be arcuate (e.g., arcuately concave) and/or planar. The outer side of the teeth 62 may planar and/or arcuate (e.g., arcuately convex or concave). The teeth 32 may define an axis that is aligned with the axis of the bone anchor member 14. Stated differently, the teeth 32 may extend along a direction that is aligned or parallel to the axis of the bone anchor member 14 (and thereby perpendicular or normal to the head portion 46).

As also shown in FIGS. 1, 2, 5, 6, 14 and 18, the peripheral row of teeth 62 may be angled laterally or annularly/circumferentially. The teeth 62 may be "aggressive" such that the teeth 62 (e.g., the front faces thereof) are oriented at an acute angle. The teeth 62 may be oriented (e.g., angled) annularly/circumferentially in a direction that opposes the direction of the thread of the shaft portion 48. In this way, the teeth 62 may be configured to dig into bone and resist rotation of the bone anchor member 14 in a direction that would unscrew or threadably de-couple from the threaded shaft 18 of the tack member 12 (when coupled therewith and implanted/installed in/on a bone).

Figure 25:
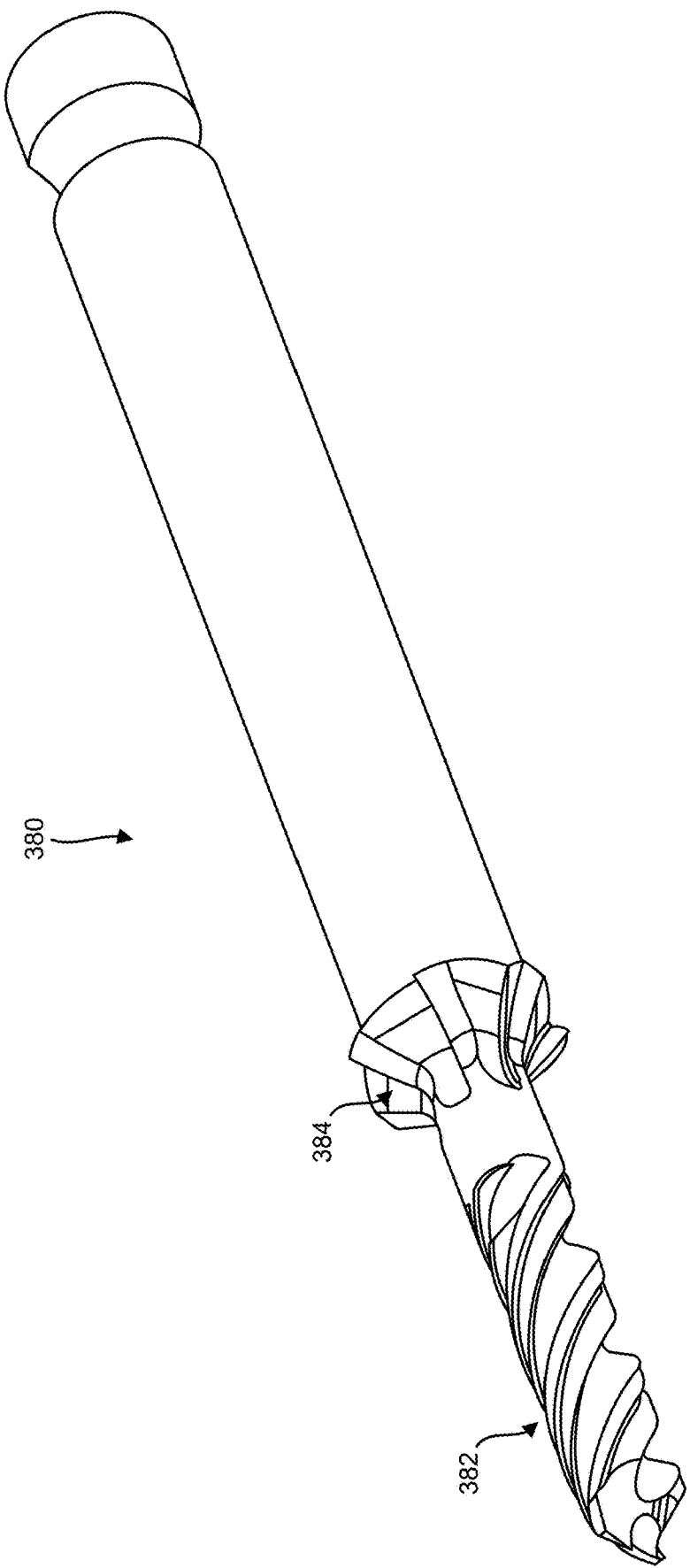
FIG. 25 illustrates a perspective view of an exemplary drill bit for preparing a counter-sunk through hole in a bone for use with the soft tissue and bone retention device of FIGS. 1-7, in accordance with an aspect of the present disclosure.
Figure 26:
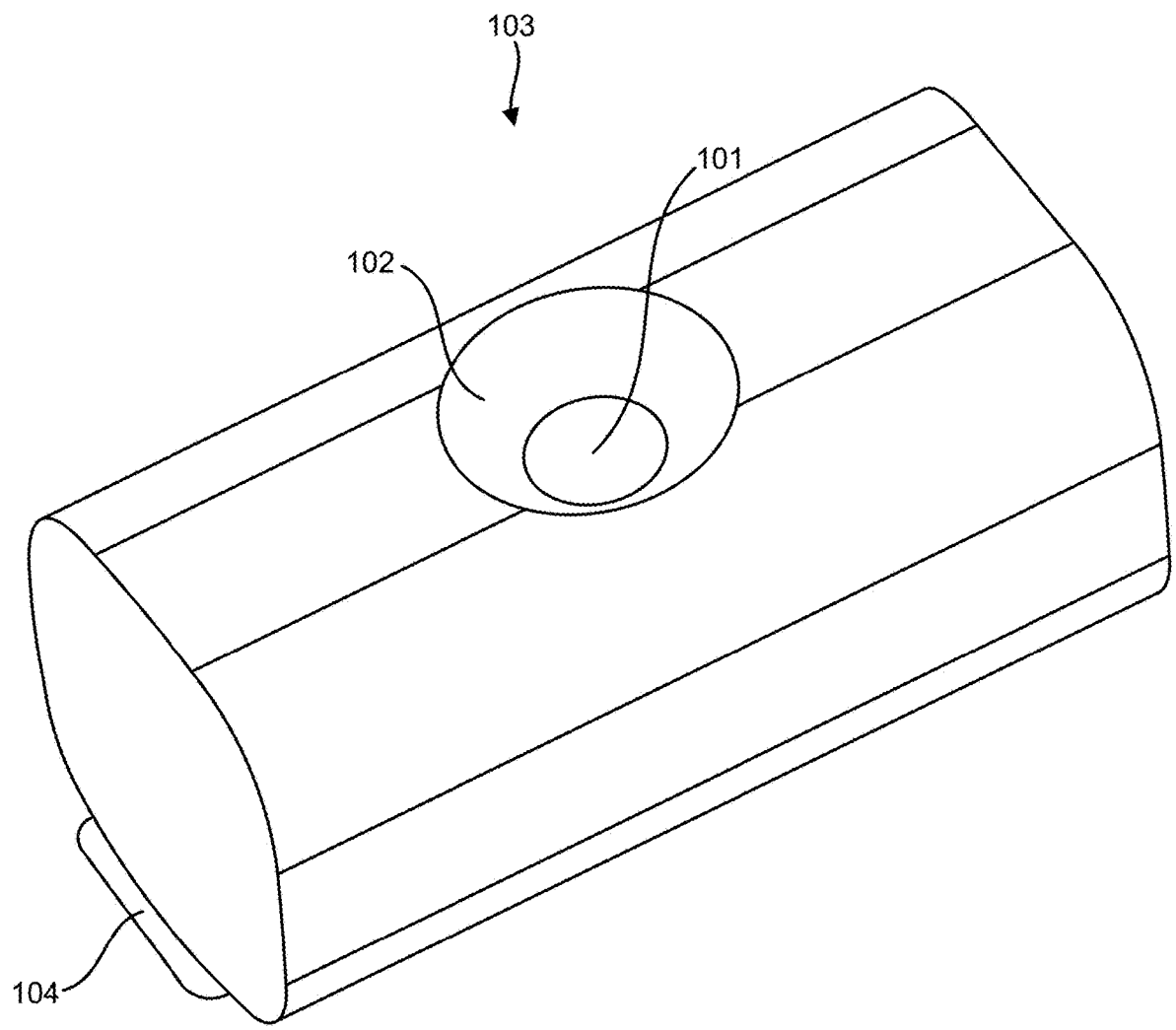
FIG. 26 illustrates an elevational perspective view of an exemplary bone with a counter-sunk through hole prepared via the drill bit of FIG. 25 and adjacent soft tissue, in accordance with an aspect of the present disclosure.

An exemplary soft tissue retention drill bit 180 as shown in FIG. 25 may be utilized to form a soft tissue retention aperture 101 in a bone 100 as shown in FIG. 26. As shown in FIGS. 25 and 26, the drill bit 180 may include an aperture or through hole cutting portion 182 configured to form the aperture or through hole 101 that extends through the bone 100 via rotation of the cutting portion 182. As also shown in FIGS. 25 and 26, the drill bit 180 may include a countersink portion 184 that is configured to form a countersink 102 in through hole 101 on the side of the bone 100 that opposes soft tissue 104 via rotation of the countersink portion 184.

The cannulated opening 40 and drive aperture 24 of the soft tissue tack member 12, and the cannulated opening 40 and drive aperture 54 of the bone anchor member 14, may facilitate assembly and implantation of the soft tissue retention device 10 via instrumentation, as shown in FIGS. 19-31. An exemplary tack member drive and guide instrument 170 configured to facilitate assembly and implantation of the soft tissue retention device 10, and the selection of a properly sized bone anchor member 14 for a specific bone 100, is shown in FIGS. 19-21 and 29-31.

As shown in FIGS. 19-21 and 29-31, the tack member drive and guide instrument 170 includes a guide and sizing wire, post, member or portion 171 extending from a drive or torque projection 172 at an end of a handle portion 173. As shown in FIGS. 19, 20, 29, 30, the handle portion 173 of the instrument 170 includes an aperture, annulus, ring, loop, band, or the like that allows a user to hold and manipulate the installation instrument 170, potentially with one hand. For example, the aperture of the instrument 170 may be configured (e.g., sized and shaped) to allow a user to extend a digit therethrough, such as a user's thumb. In this way, a user can extend their thumb (for example) through the aperture of the instrument 170 and use at least a portion of the rest of their hand/fingers to engage the patient (e.g., engage a portion of the patient's foot or other body portion on an opposing side of the portion engaged (indirectly or directly) by the instrument 170).

Figure 29:
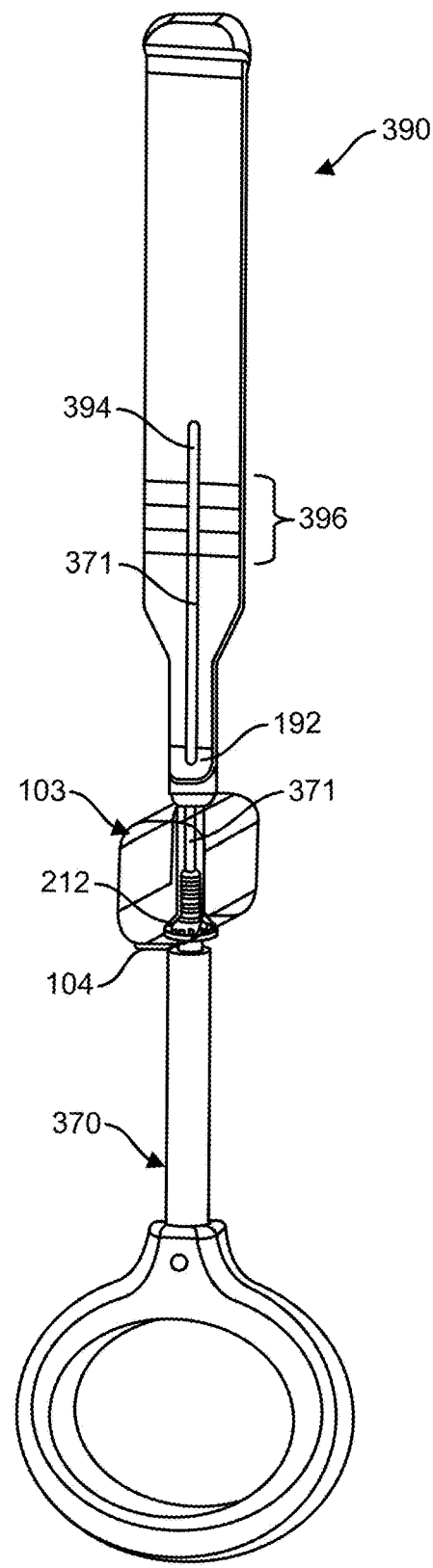
FIG. 29 illustrates a perspective view of the soft tissue tack member of FIGS. 1-7 extending through the soft tissue and held within the through hole of the prepared bone of FIG. 26 via the tack member drive and guide instrument of FIGS. 19-21 and the bone anchor member sizing guide of FIGS. 27 and 28 utilized therewith to determine a properly sized bone anchor member, in accordance with an aspect of the present disclosure.
Figure 30:
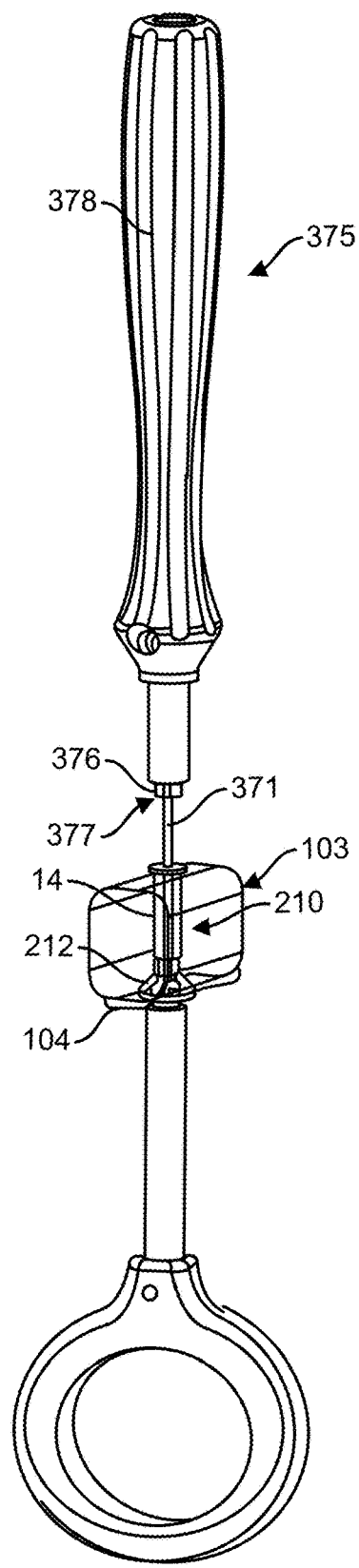
FIG. 30 illustrates a perspective view of the soft tissue tack member, the soft tissue, the prepared bone, and the tack member drive and guide instrument of FIG. 29 with the bone anchor member of FIGS. 1-7 being coupled to the soft tissue tack member within the through hole of the bone via the bone anchor member drive and guide instrument of FIGS. 22-24, in accordance with an aspect of the present disclosure.
Figure 31:
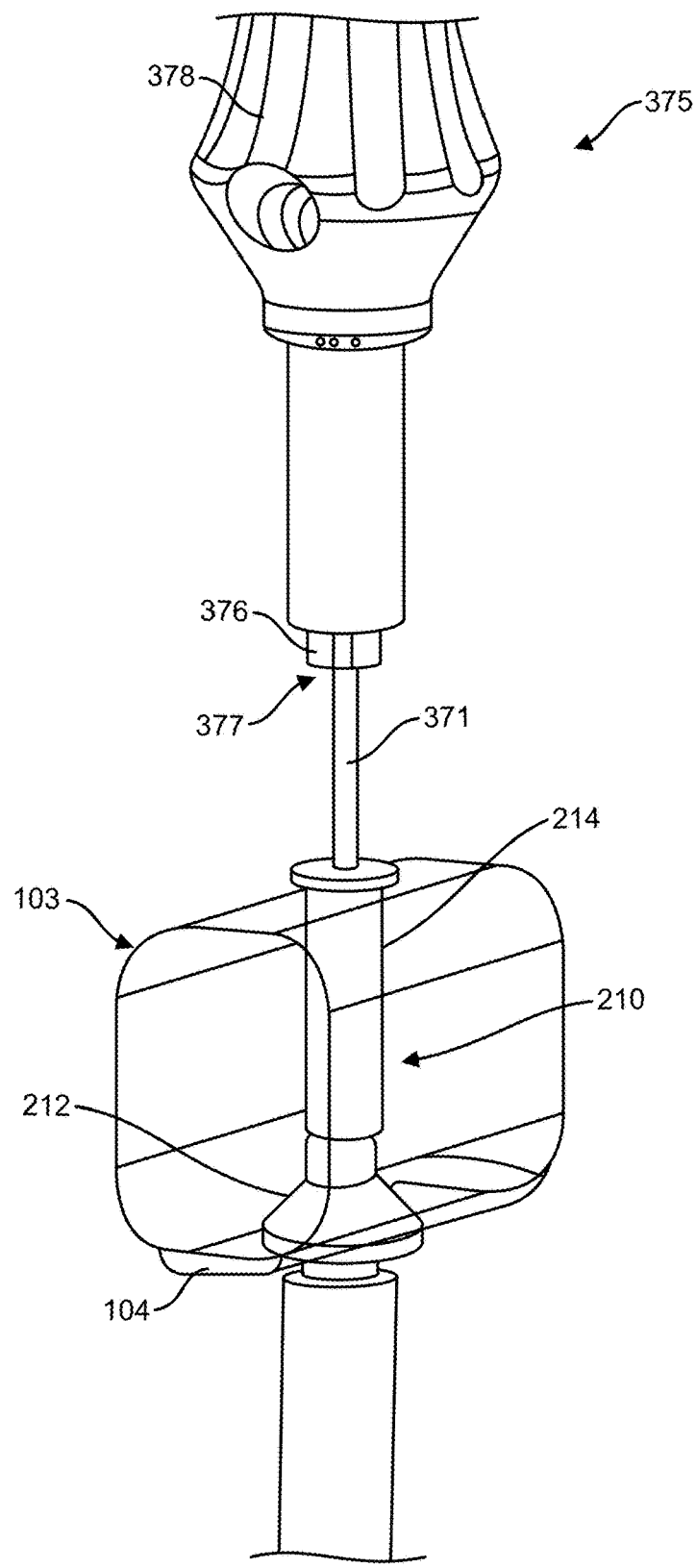
FIG. 31 illustrates an enlarged perspective view of a portion of the arrangement of the soft tissue tack member, the soft tissue, the prepared bone, the tack member drive and guide instrument and the bone anchor member drive and guide instrument of FIG. 30.
Figure 32:
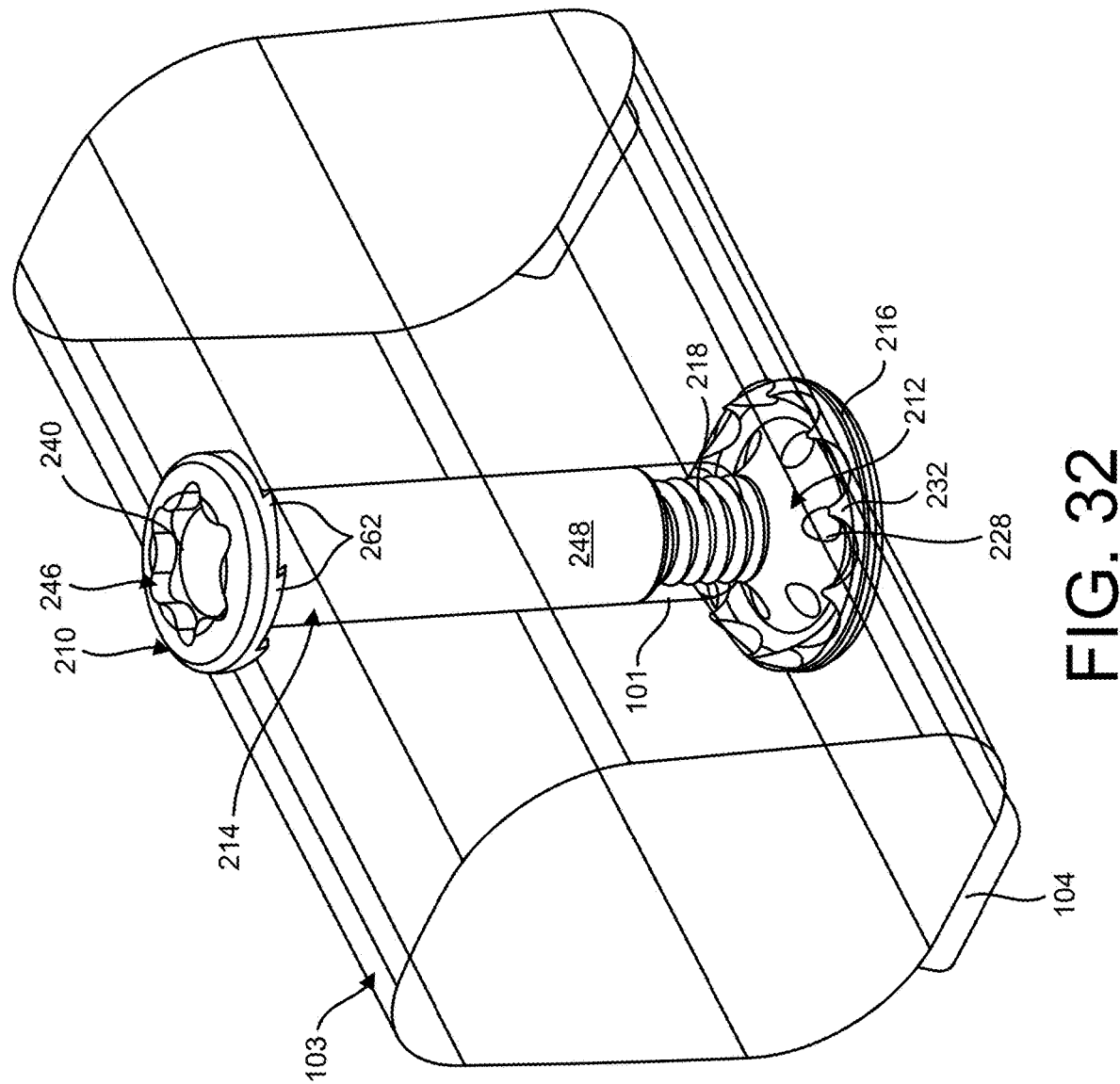
FIG. 32 illustrates an elevational perspective view of the coupled soft tissue tack member and bone anchor member retaining the soft tissue to the bone of FIGS. 30 and 31 with the instrumentation removed, in accordance with an aspect of the present disclosure.
Figure 33:
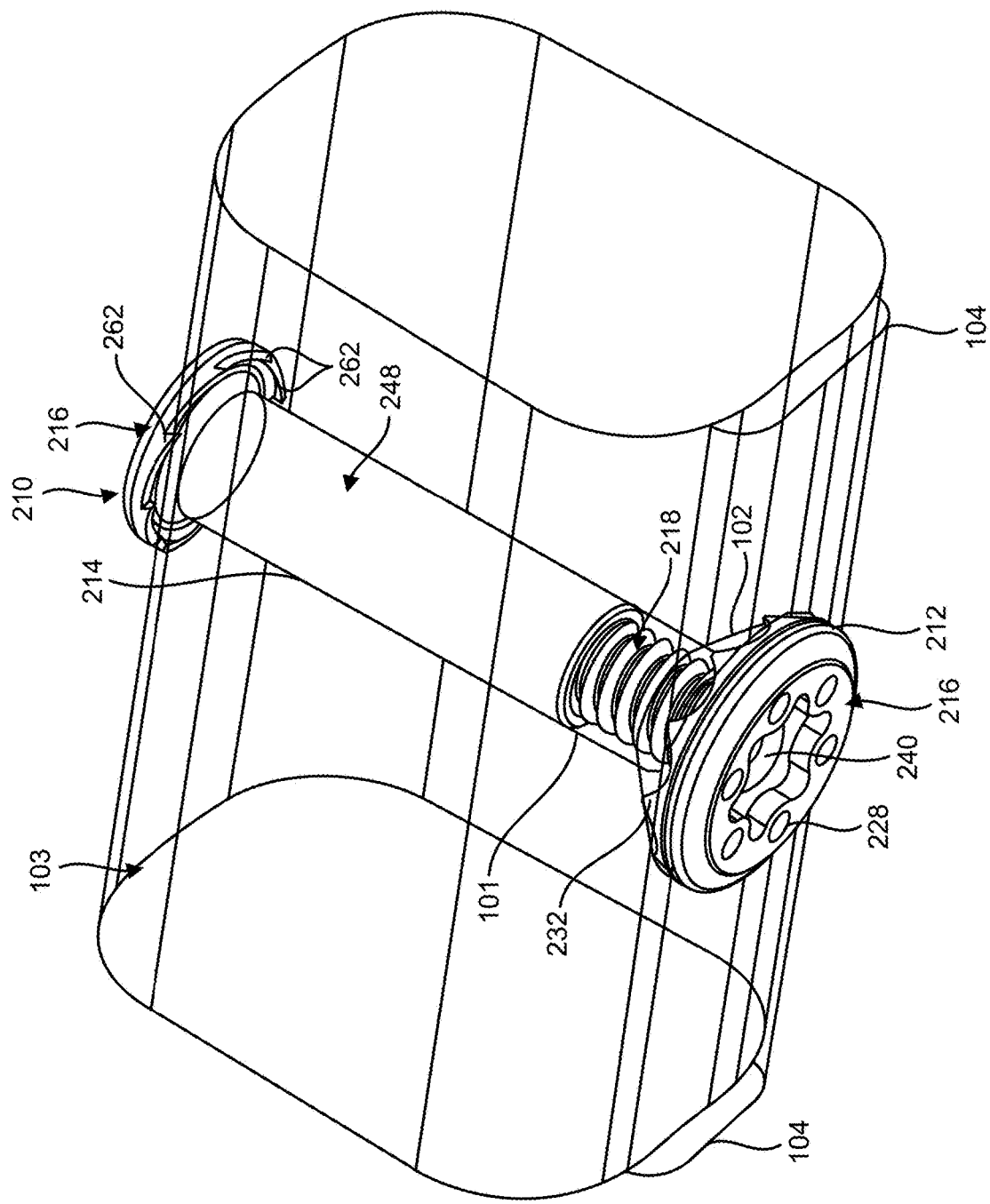
FIG. 33 illustrates a bottom perspective view of the coupled soft tissue tack member and bone anchor member retaining the soft tissue to the bone of FIG. 32.
Figure 34:
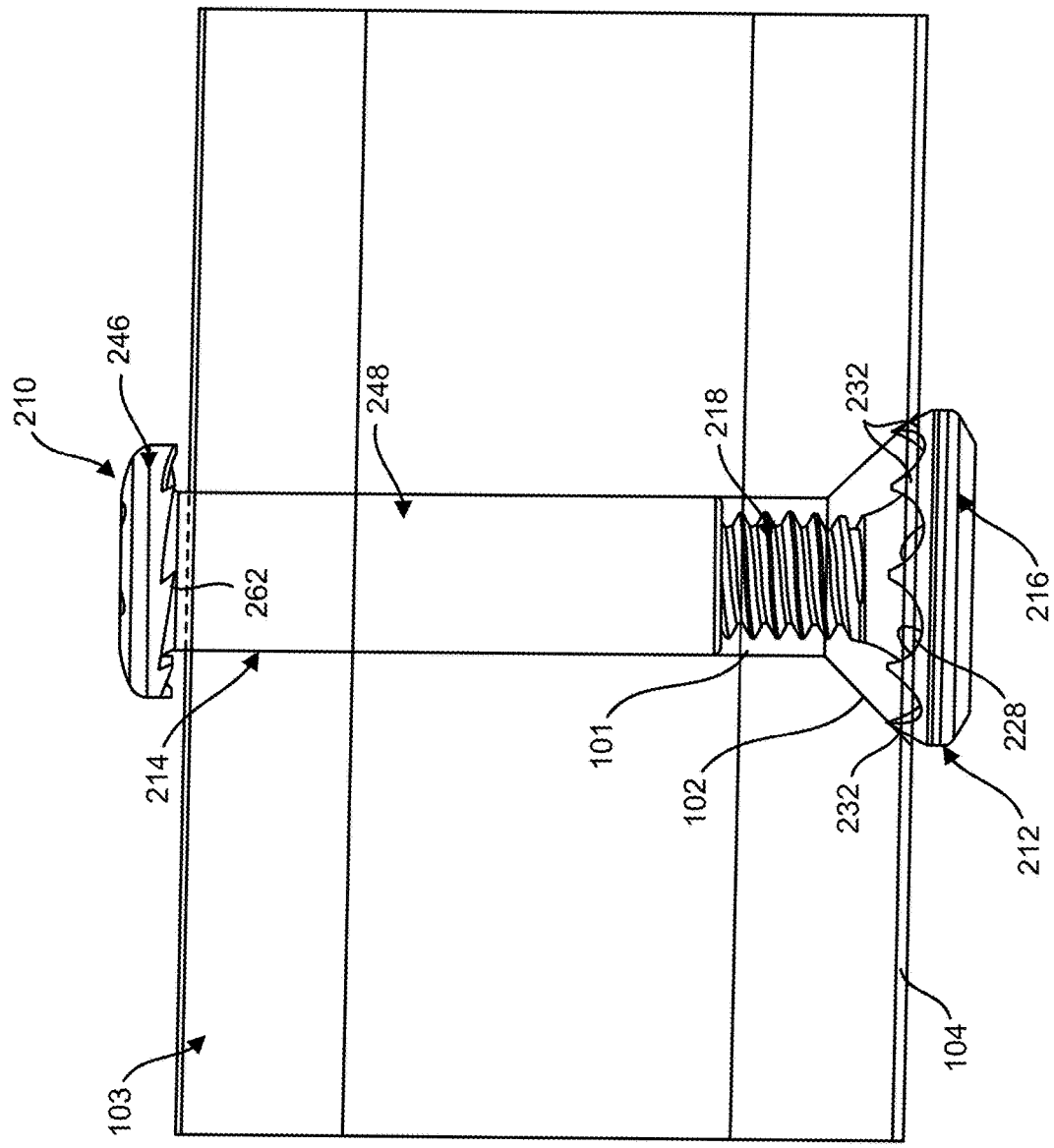
FIG. 34 illustrates a side view of the coupled soft tissue tack member and bone anchor member retaining the soft tissue to the bone of FIG. 32.
Figure 35:
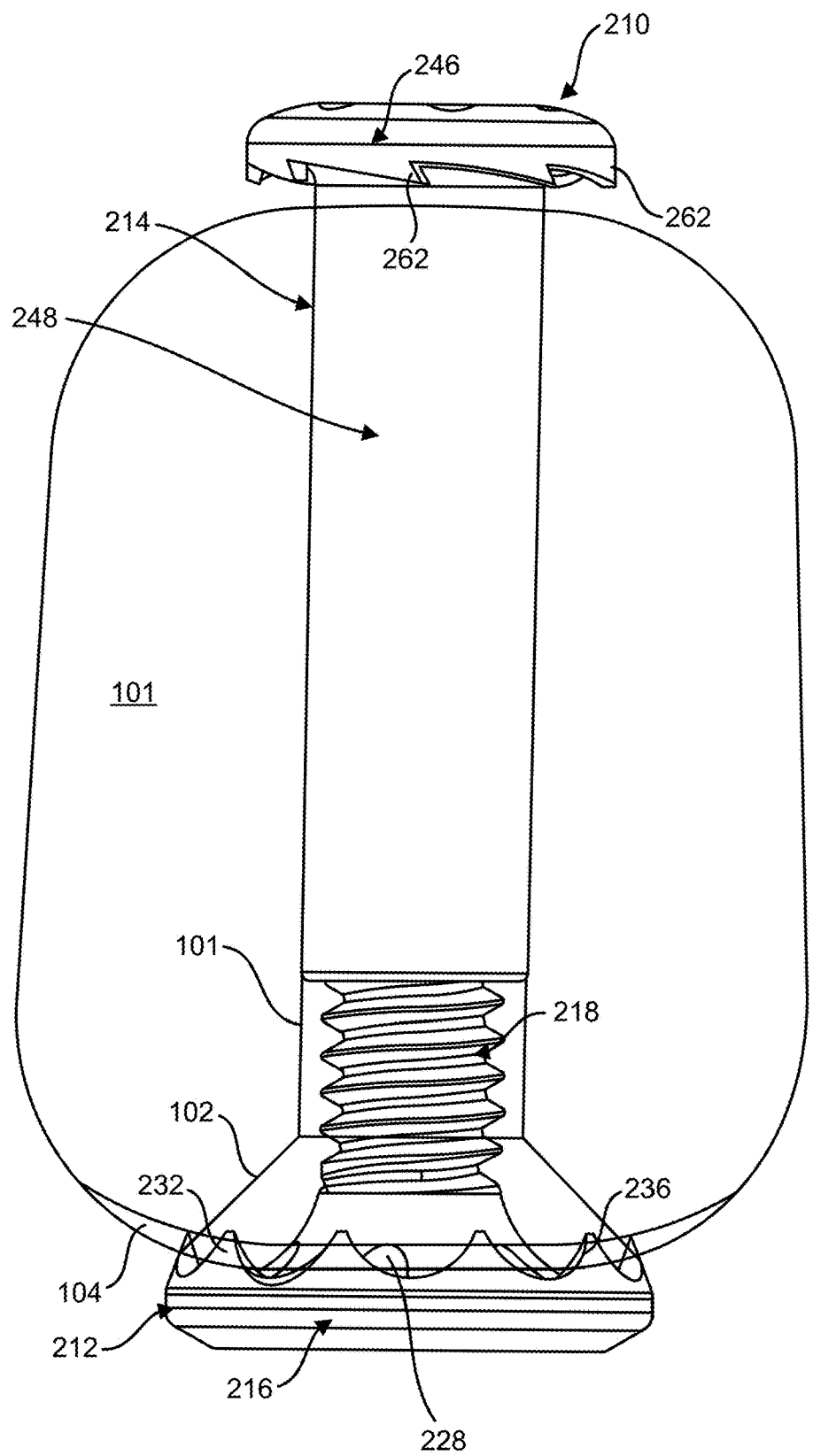
FIG. 35 illustrates an end view of the coupled soft tissue tack member and bone anchor member retaining the soft tissue to the bone of FIG. 32.

The guide and sizing wire 171 is configured to extend through the cannulated openings 40 of the soft tissue tack member 12 and the bone anchor member 14 (i.e., the cannulated opening 40 of the soft tissue retention device 10). The guide and sizing wire 171 is of a fixed pre-determined length such that the free end or tip of the wire 171 is at a fixed pre-defined distance from the drive projection 172. The drive projection 172 is configured to mate or extend within the drive aperture 24 of the soft tissue tack member 12. As such, the drive projection 172 may be of the same non-circular cross-sectional shape and size as the drive aperture 24 of the soft tissue tack member 12. The handle portion 173 may be fixed to the drive projection 172 such that torque/rotation (e.g., manual rotation) of the handle portion 173 rotates the drive projection 172 (or that prevention of rotation of the handle portion 173 prevents rotation of the drive projection 172). In this way, as shown in FIGS. 29-31, the tack member drive and guide instrument 170 may be manipulated such that the guide and sizing wire 171 is passed/positioned into and through the cannulated opening 40 of the soft tissue tack member 12 (from the head portion 16 thereof) and the drive projection 172 is positioned/mated within the drive aperture 24. The handle portion 173 can then be utilized to support and manipulate the soft tissue tack member 12 to position the soft tissue tack member 12 through soft tissue and into the aperture 101 of the bone 100 with the guide wire portion 171 extending through the aperture 101, and to ultimately rotate/apply torque to the soft tissue tack member 12 (or prevent rotation thereof), as shown in FIGS. 29-31.

Figure 22:
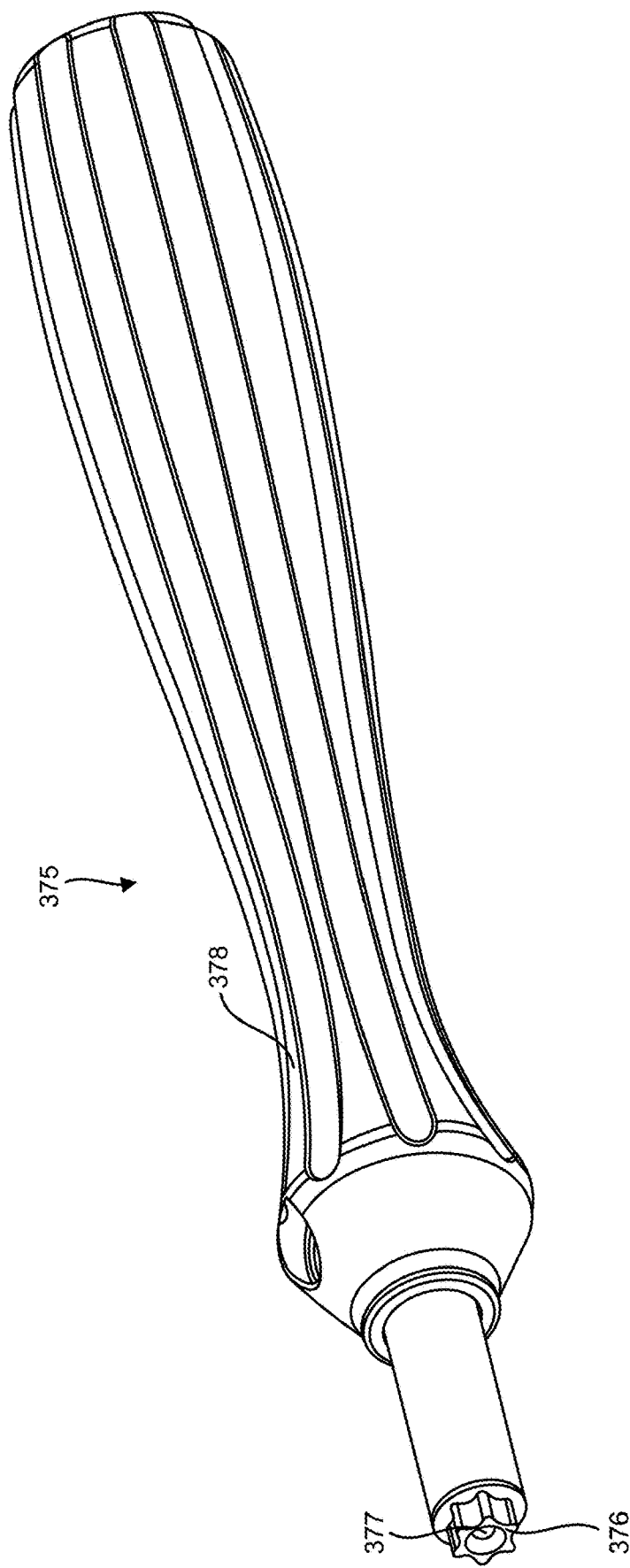
FIG. 22 illustrates a perspective view of an exemplary bone anchor member drive and guide instrument, in accordance with an aspect of the present disclosure.
Figure 23:
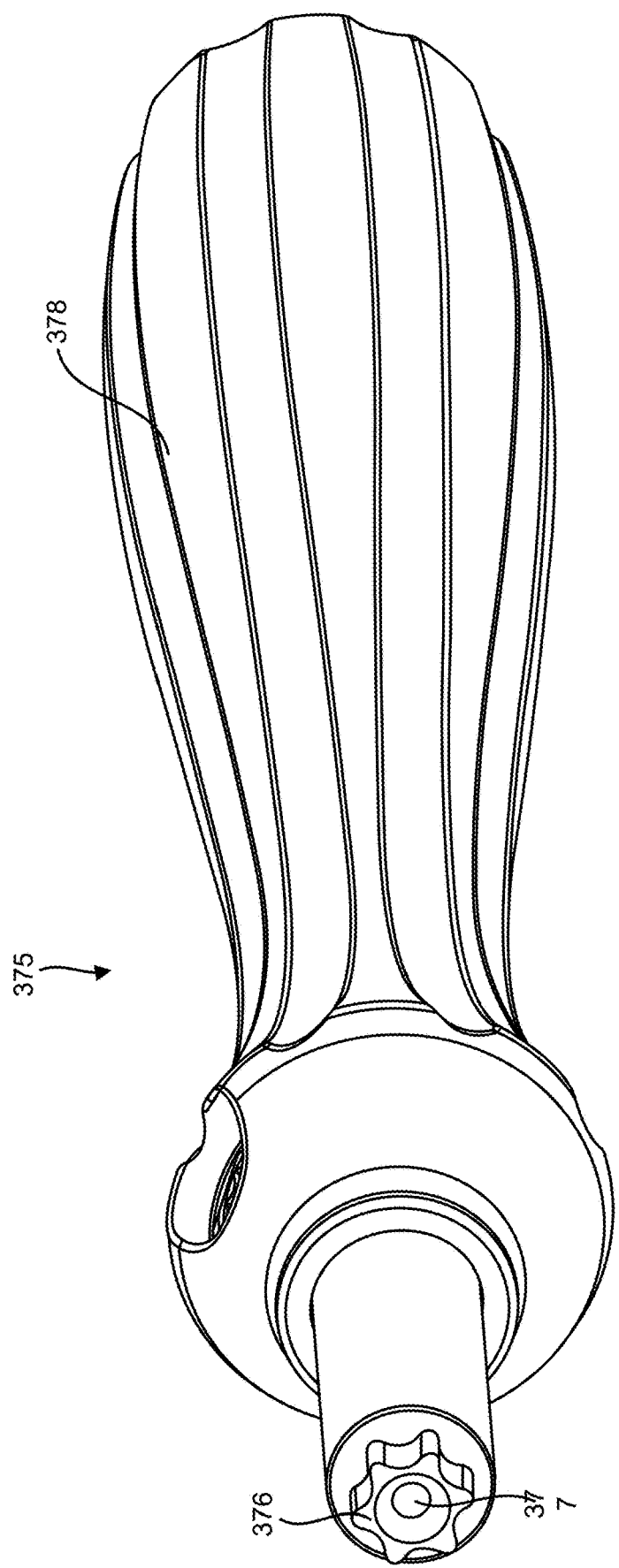
FIG. 23 illustrates another perspective view of the bone anchor member drive and guide instrument of FIG. 22.
Figure 24:
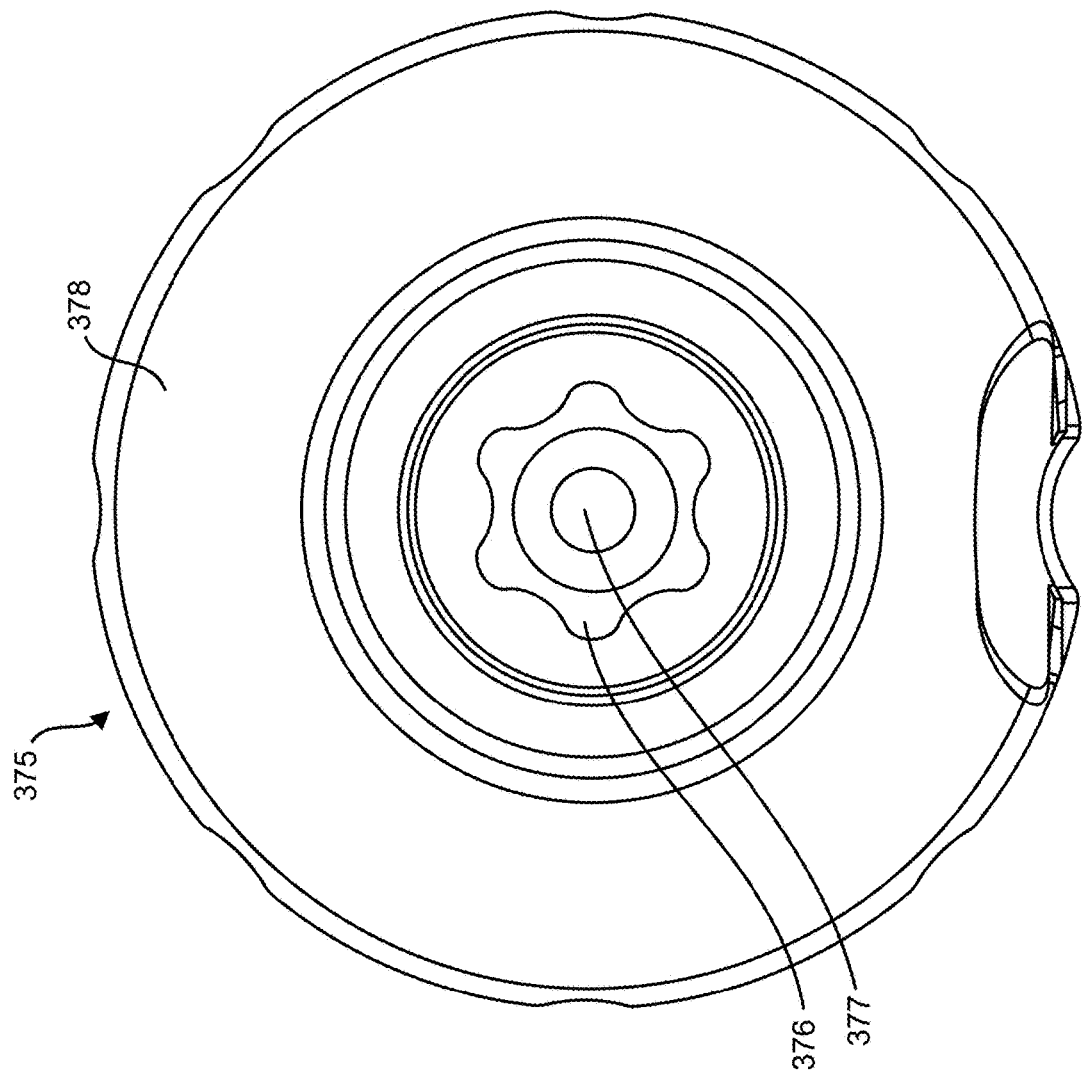
FIG. 24 illustrates a drive end view of the bone anchor member drive and guide instrument of FIG. 22.

An exemplary bone anchor member drive and guide instrument 175 configured to facilitate assembly and implantation of the soft tissue retention device 10 is shown in FIGS. 22-24, 30 and 31. As shown in FIGS. 22-24, 30 and 31, the anchor member drive and guide instrument 175 includes a drive or torque projection 176 provided at an end of a handle portion 178. As shown in FIGS. 22-24, the anchor member drive and guide instrument 175 also includes a cavity or opening 177 extending from and into the drive projection 176 that is configured to accept or house the guide and sizing wire 171 of the tack member drive and guide instrument 170 therein. In this way, the cavity 177 of the anchor member drive and guide instrument 175 is configured to allow the guide and sizing wire 171 of the tack member drive and guide instrument 170 to extend therein.

The drive projection 176 is configured to mate or extend within the drive aperture 54 of the bone anchor member 14. As such, the drive projection 176 may be of the same non-circular cross-sectional shape and size as the drive aperture 54 of the bone anchor member 14. The handle portion 178 may be fixed to the drive projection 176 such that torque/rotation (e.g., manual rotation) of the handle portion 178 rotates the drive projection 176 (or that prevention of rotation of the handle portion 178 prevents rotation of the drive projection 176). In this way, as shown in FIGS. 30 and 31, the bone anchor member drive and guide instrument 175 (and the tack member drive and guide instrument 170) may be manipulated such that the drive projection 176 is positioned/mated within the drive aperture 54 of the bone anchor member 14. The handle portion 178 can then be utilized to support and manipulate the bone anchor member 14 to position the guide and sizing wire 171 of the tack member drive and guide instrument 170 into the cavity 177 of the bone anchor member drive and guide instrument 175 to align the soft tissue tack member 12 and the bone anchor member 14 (and align the bone anchor member 14 with the aperture 101), position the bone anchor member 14 into the aperture 101 of the bone 100, and to ultimately rotate/apply torque to the bone anchor member 14 (or prevent rotation thereof) to threadably couple the shaft portion 18 of the soft tissue tack member 12 and the shaft portion 48 of the bone anchor member 14 and compress the soft tissue retention device on the bone 100, as shown in FIGS. 30 and 31.

Figure 27:
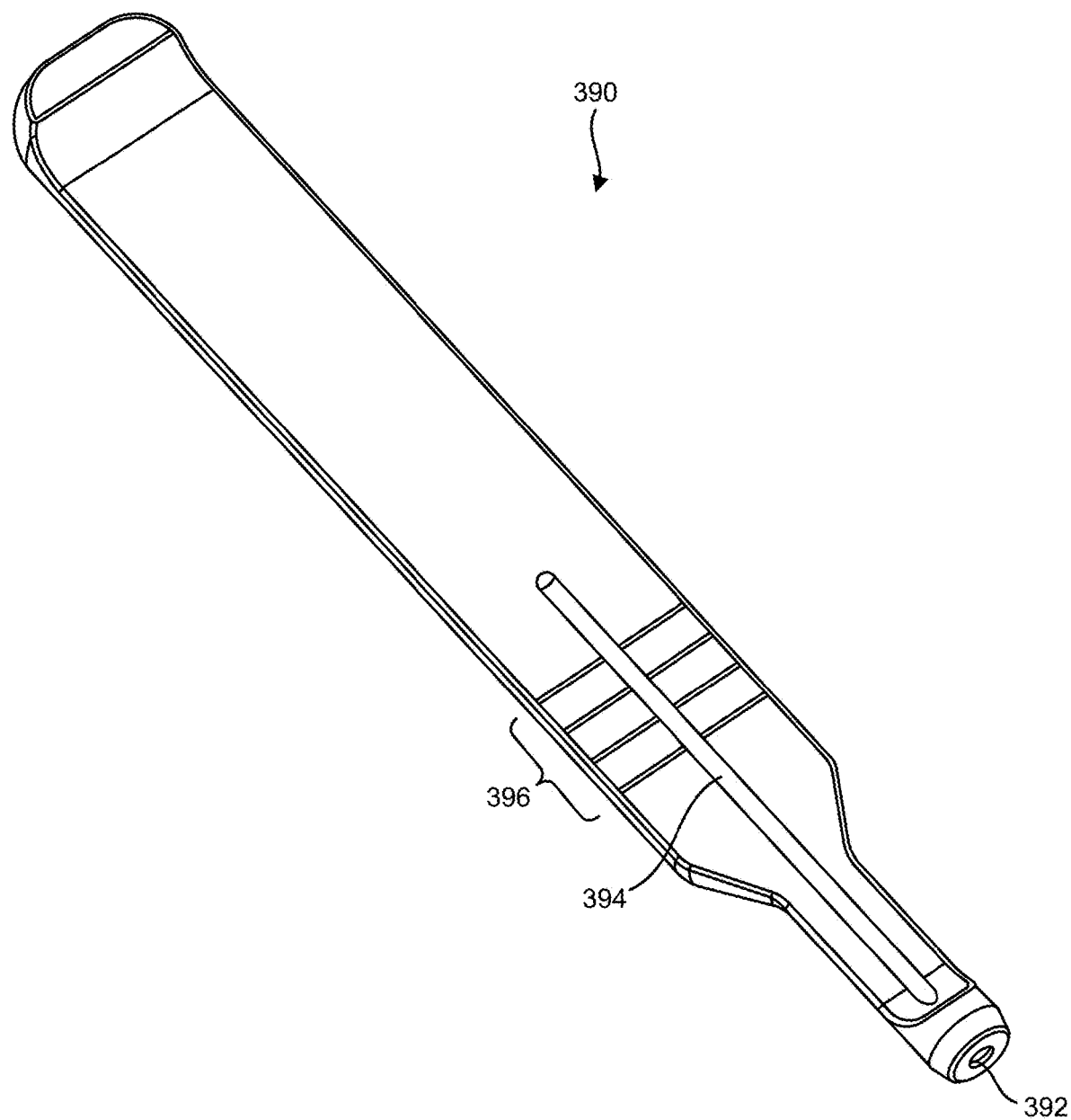
FIG. 27 illustrates an elevational perspective view of an exemplary bone anchor member sizing guide, in accordance with an aspect of the present disclosure.
Figure 28:
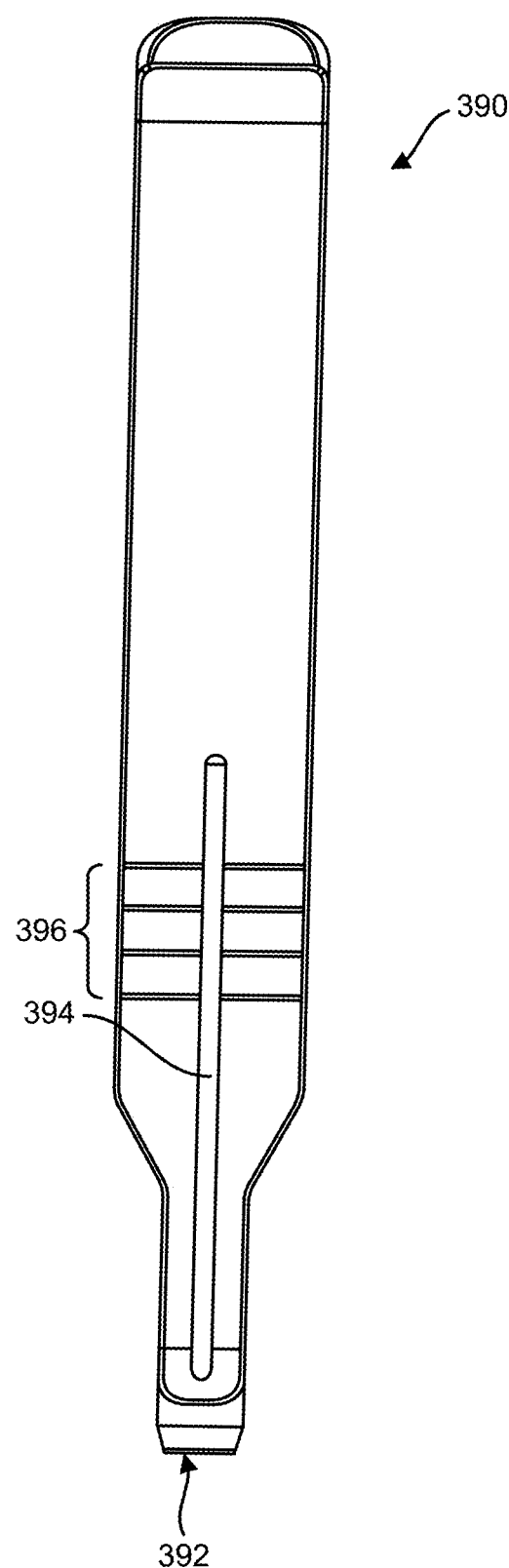
FIG. 28 illustrates a front view of the bone anchor member sizing guide of FIG. 27.

As noted above, the tack member drive and guide instrument 170 may be utilized to facilitate the selection/determination of a properly sized bone anchor member 14 for the specific bone 100. As shown in FIGS. 27-29, a bone anchor member sizing guide 190 may be configured to be utilized with the tack member drive and guide instrument 170 to facilitate the selection/determination of a properly sized bone anchor member 14 for the specific bone 100. The bone anchor member sizing guide 190 may include an opening or through hole/aperture 192 at an end or tip of the bone anchor member sizing guide 190 that is configured to accept the wire portion 171 of the tack member drive and guide instrument 170 therein/therethrough (see FIG. 29). The bone anchor member sizing guide 190 may also include a groove, indentation and/or marking 194 that aligns with and accepts the portion of the wire portion 171 of the tack member drive and guide instrument 170 that passes through the opening 192, as shown in FIG. 29. As shown in FIG. 29, the bone anchor member sizing guide 190 also includes a plurality of sizing markings 196 proximate to the groove 194 that correspond to differently sized bone anchor members 14. For example, the plurality of sizing markings 196 of the bone anchor member sizing guide 190 may correspond to bone anchor members 14 with differing axial/longitudally sized shaft portions 48 (with the head portions 46 being of the same size or different sizes).

As shown in FIG. 29, the bone anchor member sizing guide 190 may thereby be utilized to determine a properly sized bone anchor member 14 for a bone 100 which includes the soft tissue tack member 12 positioned in the through aperture 101 thereof (and through soft tissue) (such as on/in abutment with the countersink 102 in the bone 100) via the tack member drive and guide instrument 170. The tip or end of the bone anchor member sizing guide 190 may be positioned on/in abutment with the opposing side of the bone 100 as the soft tissue and soft tissue tack member 12 with the wire portion 171 of the tack member drive and guide instrument 170 extending through the opening 192 and along the groove 194, as shown in FIG. 29. The end of the wire portion 171 of the tack member drive and guide instrument 170 may substantially align (or most closely align) with one of the size indications 196. The size indications 196 thereby indicate how thick the bone 100 is (or how thick/long the through aperture 101 is), and a correspondingly sized bone anchor member 14 that is configured to extend through the aperture 101 and to the soft tissue tack member 12 (to threadably mate with the soft tissue tack member 12, as discussed above), as shown in FIGS. 29-31.

As shown in FIGS. 32-35, with a properly sized bone anchor member 14 selected/determined, the bone anchor member 14 may be threadably coupled to the soft tissue tack member 12 and the torqued/drawn together (via rotation) to compress the head portion 16 of the soft tissue tack member 12 against the soft tissue 104 (see FIGS. 34 and 35) and bone 100 and the head portion 46 of the bone anchor member 14 against the bone 100. As noted above, the teeth 32 of the head portion 16 of the soft tissue tack member 12 may engage (and potentially penetrate into) the soft tissue 104 (and potentially the bone 100) to retain the soft tissue 104 (see FIGS. 34 and 35), and the teeth 62 of the bone anchor member 14 may engage (and potentially penetrate into) the bone 100, when the bone anchor member 14 and the soft tissue tack member 12 are torqued/drawn together as shown in FIGS. 32-35. As also discussed above, the through holes 28 in the head portion 16 of the soft tissue tack member 12 may allow the soft tissue 104 (see FIGS. 34 and 35) to extend therein to securely retain the soft tissue 104 when the bone anchor member 14 and the soft tissue tack member 12 are torqued/drawn together, as shown in FIGS. 32-35.

Another exemplary drive and guide instrument 205 configured to facilitate assembly and implantation of a soft tissue retention device is shown in FIGS. 36-42. The instrument 205 is configured for installing or implanting a soft tissue retention device into soft tissue (e.g., a tendon or ligament) and bone, such as into at least one tendon and a bone of the extremities during a tendon to bone attachment procedure. The installation instrument (instrument) 205 is depicted in in FIGS. 36-42 and described herein in conjunction with the attachment of a flexor digitorum longus tendon and an associated bone, such as, but not limited to, the plantar aspect of a proximal phalangeal base (bone). However, it is noted that the instrument 205 may be utilized with other soft tissue (e.g., ligament or tendon) and bones (i.e., other soft tissue-to-bone attachment procedures). In some embodiments, the instrument 205 is made from one or more suitable surgical grade materials such as, but not limited to, stainless steel. Scaled instruments, for scaled soft tissue retention devices/implants (or portions or members thereof) and/or patient for example, are contemplated. Such scaled instruments and scaled soft tissue retention devices/implants (or portions or members thereof) may form at least part of an installation/implantation set or kit (not shown).

The drive and guide instrument 205 may be particularly advantageous in facilitating assembly and implantation of a non-cannulated or partially-cannulated soft tissue retention device, such as a partially-cannulated soft tissue retention device disclosed in the '780 application, the '450 application, the '789 application, the '100 application and/or the '574 application. In some such embodiments, the drive and guide instrument 205 may be configured to facilitate assembly and implantation of a soft tissue retention device that includes a cannulated soft tissue tack member or portion and a non-cannulated or partially-cannulated bone anchor member or portion. However, the drive and guide instrument 205 may be configured to facilitate assembly and implantation of a fully cannulated soft tissue retention device 10 of FIGS. 1-7, such as the fully cannulated soft tissue retention device 10 of FIGS. 1-7 for example.

As shown in FIGS. 36-42, the instrument 205 includes a handle section 206 configured to allow a user to hold and manipulate the installation instrument 205 with one hand, a gauging portion 208 extending from one side of the handle section 206, and an insertion and fixation portion 210 extending from another side of the handle section 206. The gauging portion 208 is configured to aid in determining (e.g., gauging) the size of a soft tissue retention device/implant to use with a particular soft tissue and bone complex. The insertion and fixation portion 210 is configured to temporarily hold at least a portion of the retention implant during the insertion and attachment procedure. The handle section 206 may also include more implements for more functions extending therefrom.

The installation instrument 205 allows for one-handed fixation and compression of the retention implant. As shown in FIGS. 36-42, the handle section 206 comprises an aperture, annulus, ring, loop, band, or the like 212 configured (e.g., sized and shaped) to allow a user to extend a digit therethrough, such as a user's thumb. In this way, a user can extend their thumb (for example) through the aperture 212 and use at least a portion of the rest of their hand/fingers to engage the patient (e.g., engage a portion of the patient's foot or other body portion on an opposing side of the portion engaged (indirectly or directly) by the instrument 205), as explained further below and shown in FIG. 42.

Figure 36:
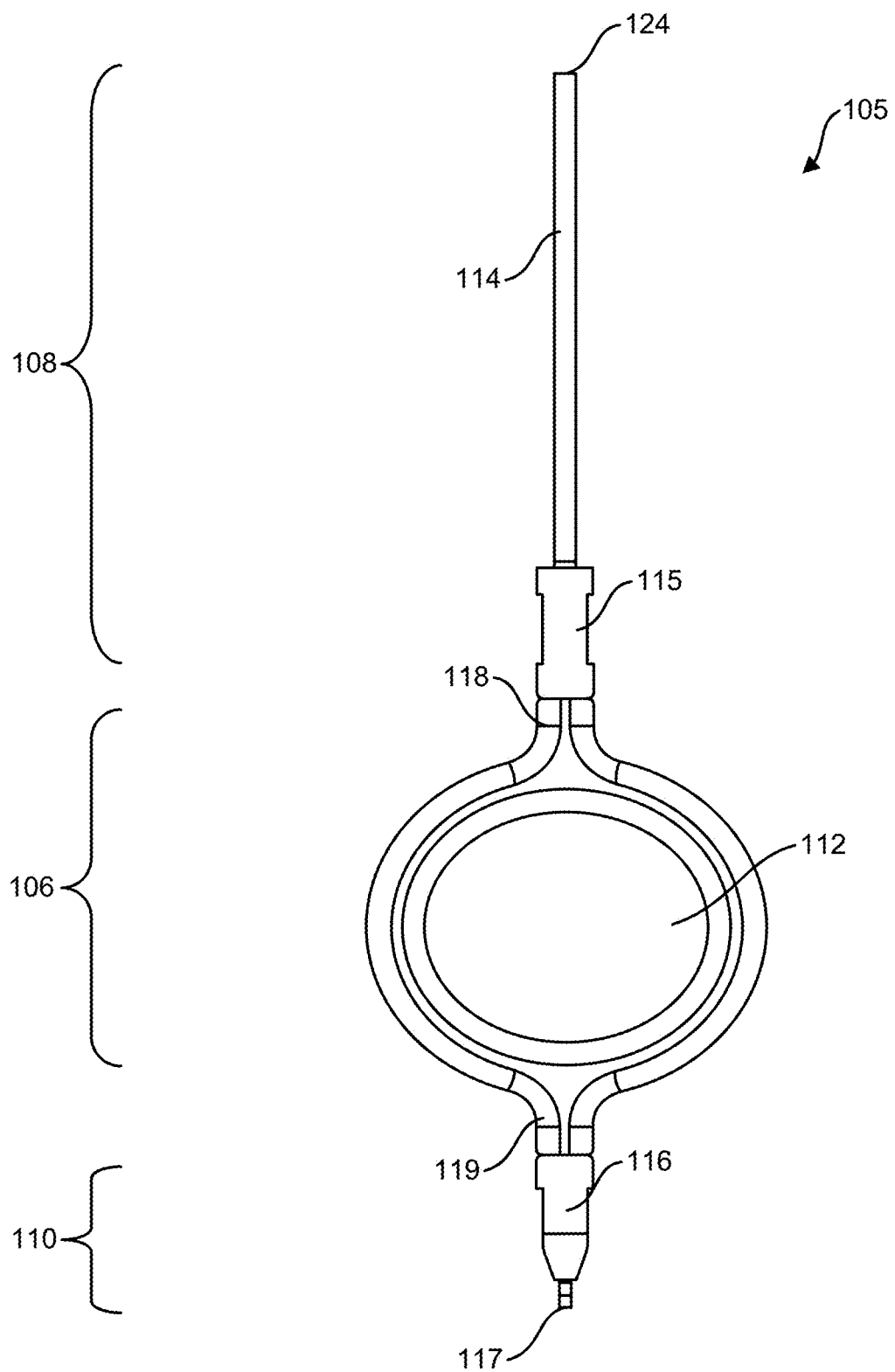
FIG. 36 illustrates an isometric view of an embodiment of an instrument for installing a soft tissue retention device during a soft tissue-to-bone attachment procedure, in accordance with an aspect of the present disclosure.
Figure 37:
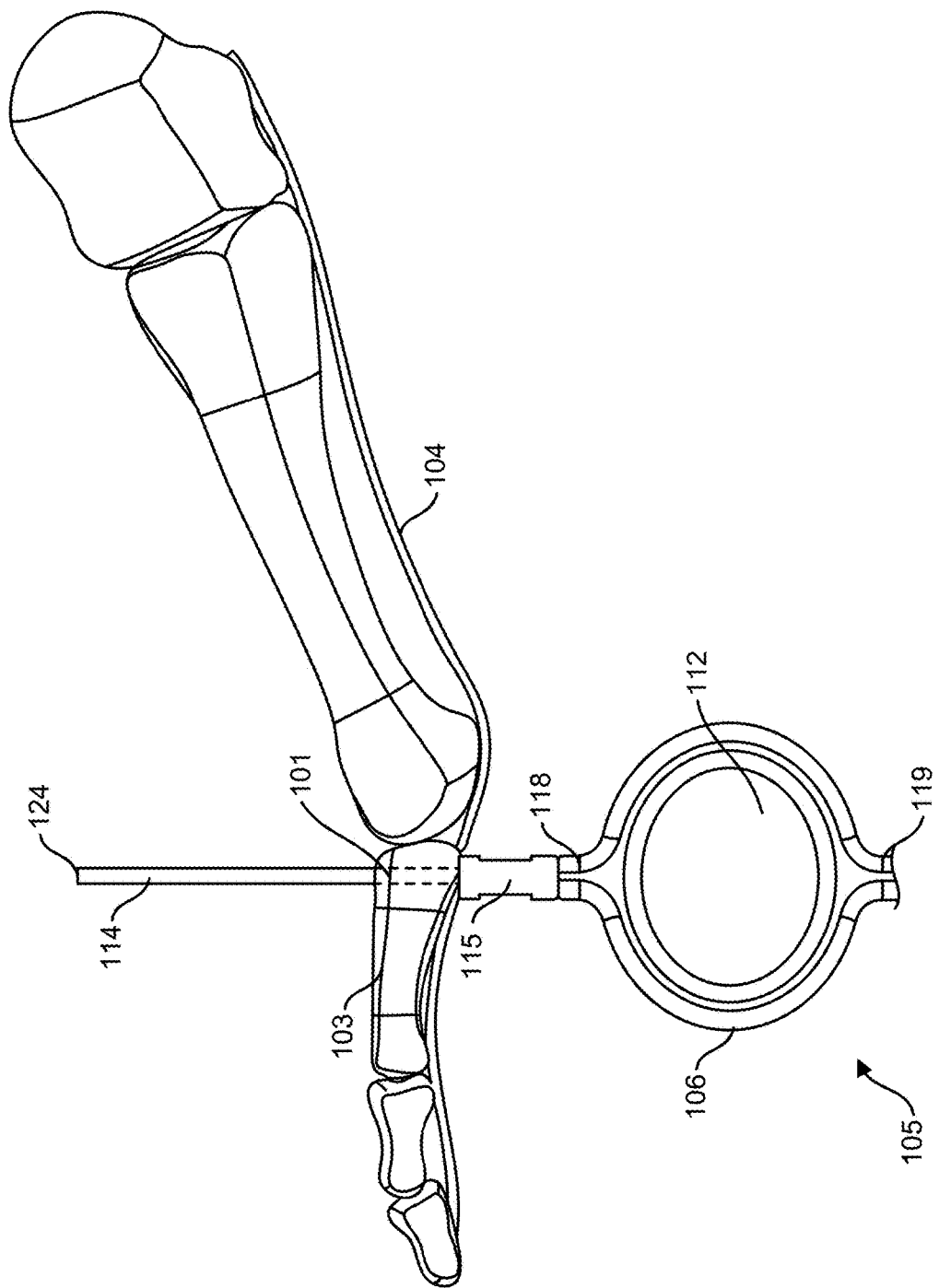
FIG. 37 illustrates a size gauging process utilizing the instrument of FIG. 36 of a soft tissue-to-bone fixation procedure for a flexor digitorum longus tendon and a proximal phalangeal base toe bone, in accordance with an aspect of the present disclosure.
Figure 38:
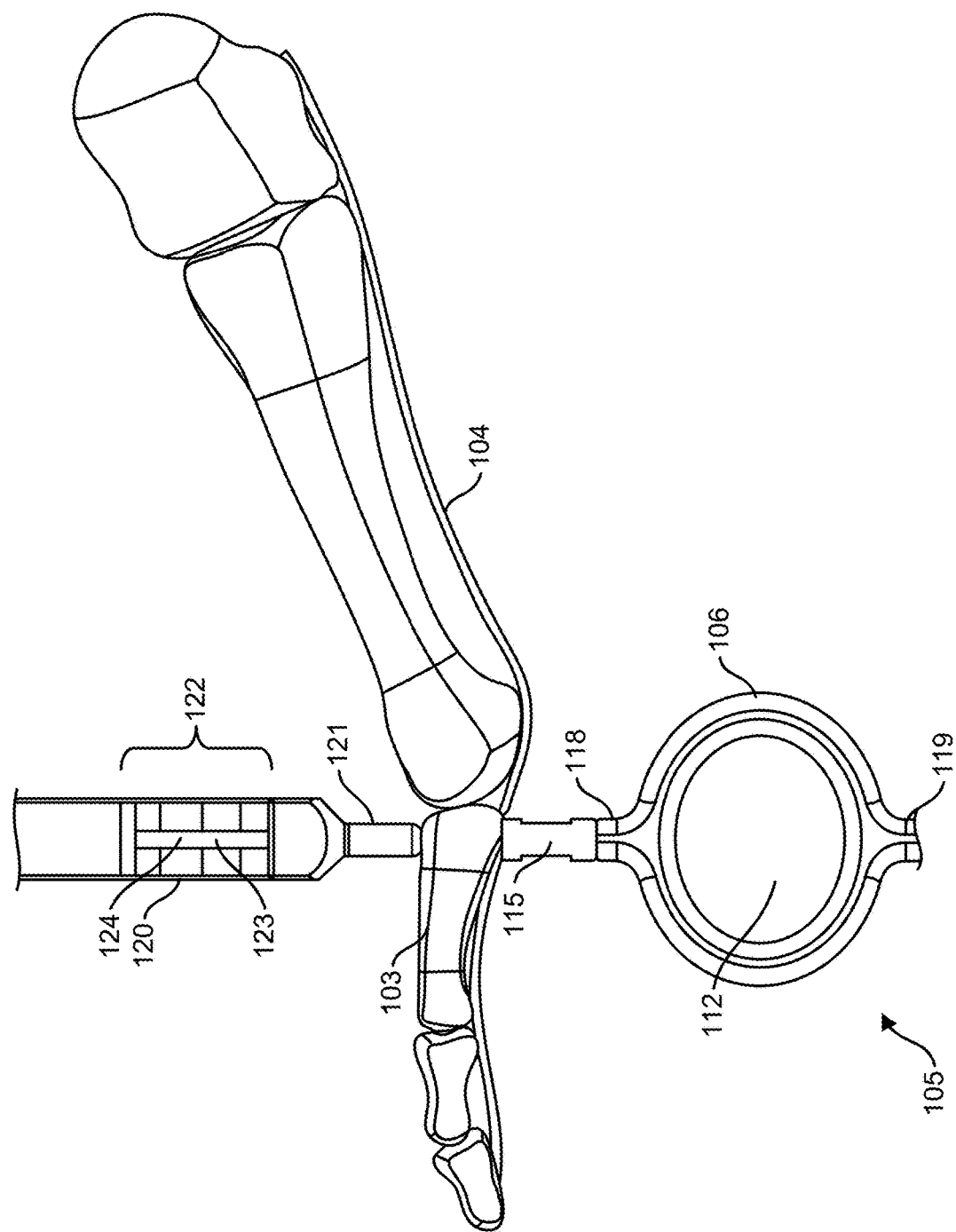
FIG. 38 illustrates the size gauging process utilizing the instrument of FIG. 36 and a size gauge of the soft tissue-to-bone fixation procedure, in accordance with an aspect of the present disclosure.

As shown in FIGS. 37 and 38, the gauging portion 208 includes a base portion 215 that extends radially from a neck portion 218 situated at one side of the handle section 206. As also shown in FIGS. 37 and 38, a rod portion 214 extends radially from the base portion 215 and defines a free end or tip 224 of the gauging portion 208. When inserted into a through hole (e.g. drilled) of a bone, the rod portion 214 aids in gauging (e.g., visually determining) an implant size to use with the particular soft tissue and bone complex, while the base 215 provides a stop/seat surface to seat against or interface with the soft tissue and/or bone. In some embodiments, as shown in FIGS. 36 and 37, the gauge rod portion 214 has a smooth outer texture. In one exemplary embodiment, the gauge rod portion 214 is cylindrical and includes a cross-sectional diameter of about 2 mm. However, other embodiments may include other configurations and/or sizes of the gauge rod portion 214.

Figure 40:
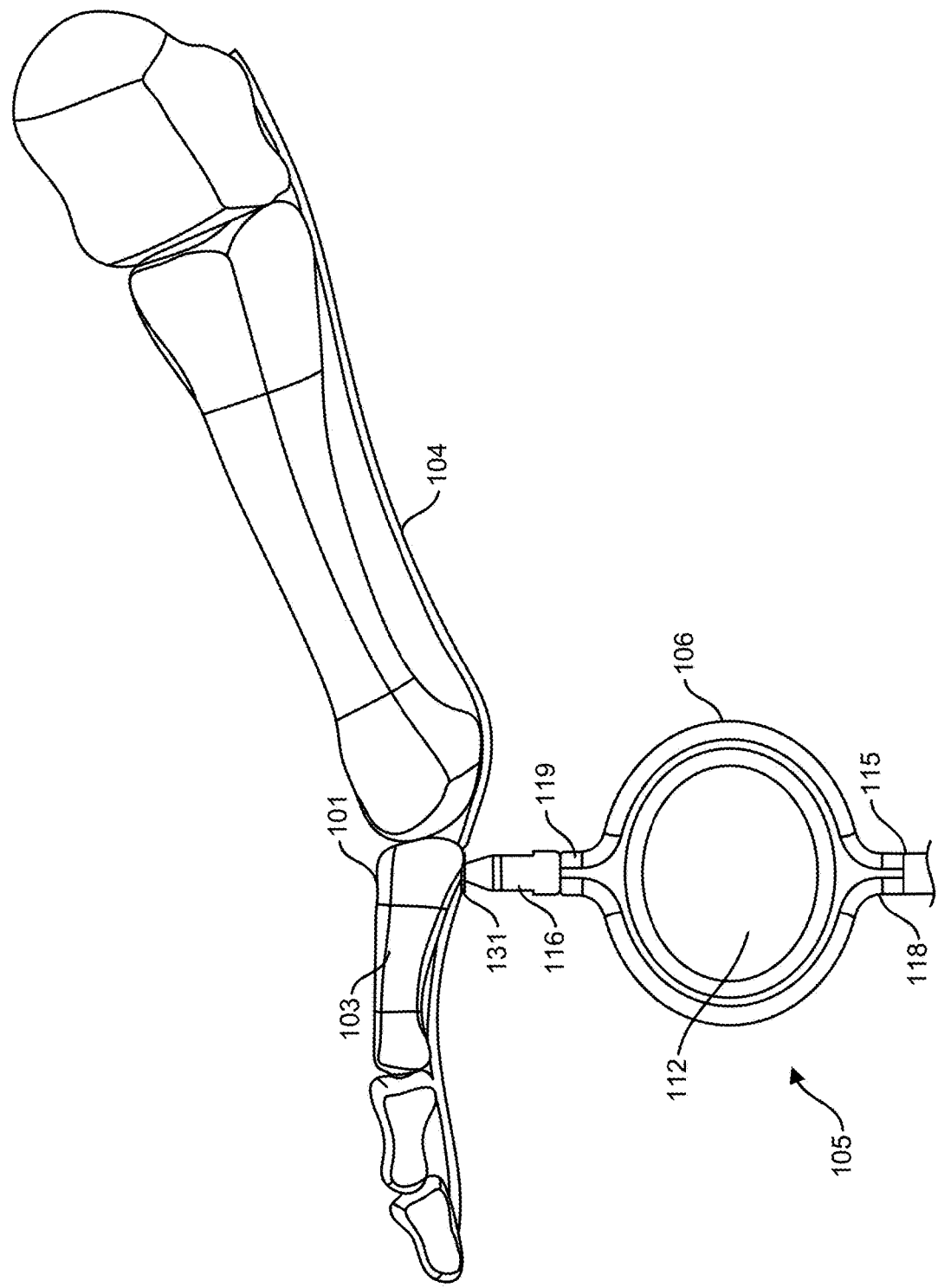
FIG. 40 illustrates the compression of the soft tissue retention tack member and the soft tissue and bone compression via the instrument of FIG. 36, in accordance with an aspect of the present disclosure.
Figure 41:
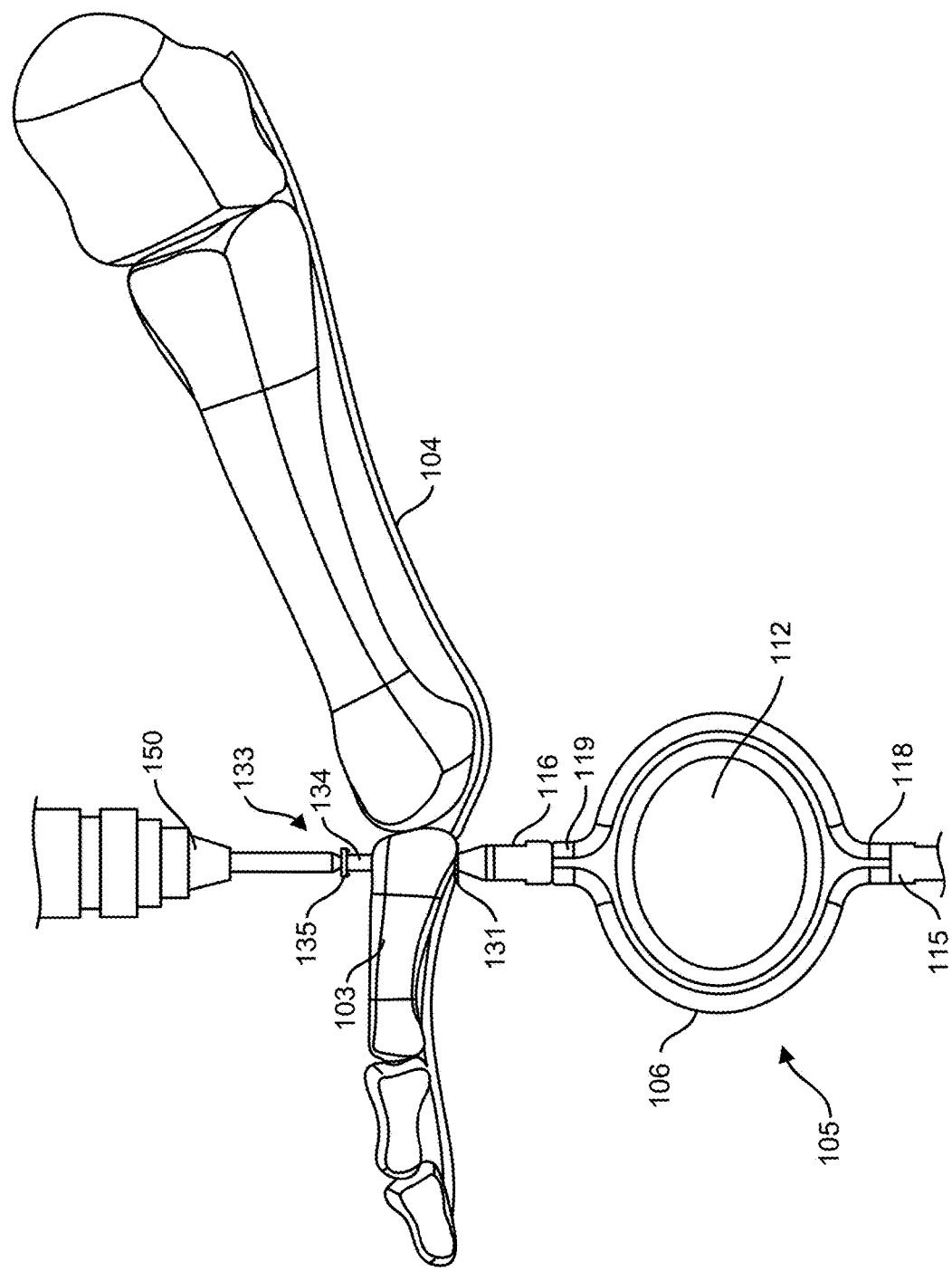
FIG. 41 illustrates the fixation of the soft tissue retention device, and the soft tissue and the bone, via threadably coupling a bone anchor member to the soft tissue retention tack member, in accordance with an aspect of the present disclosure.
Figure 42:
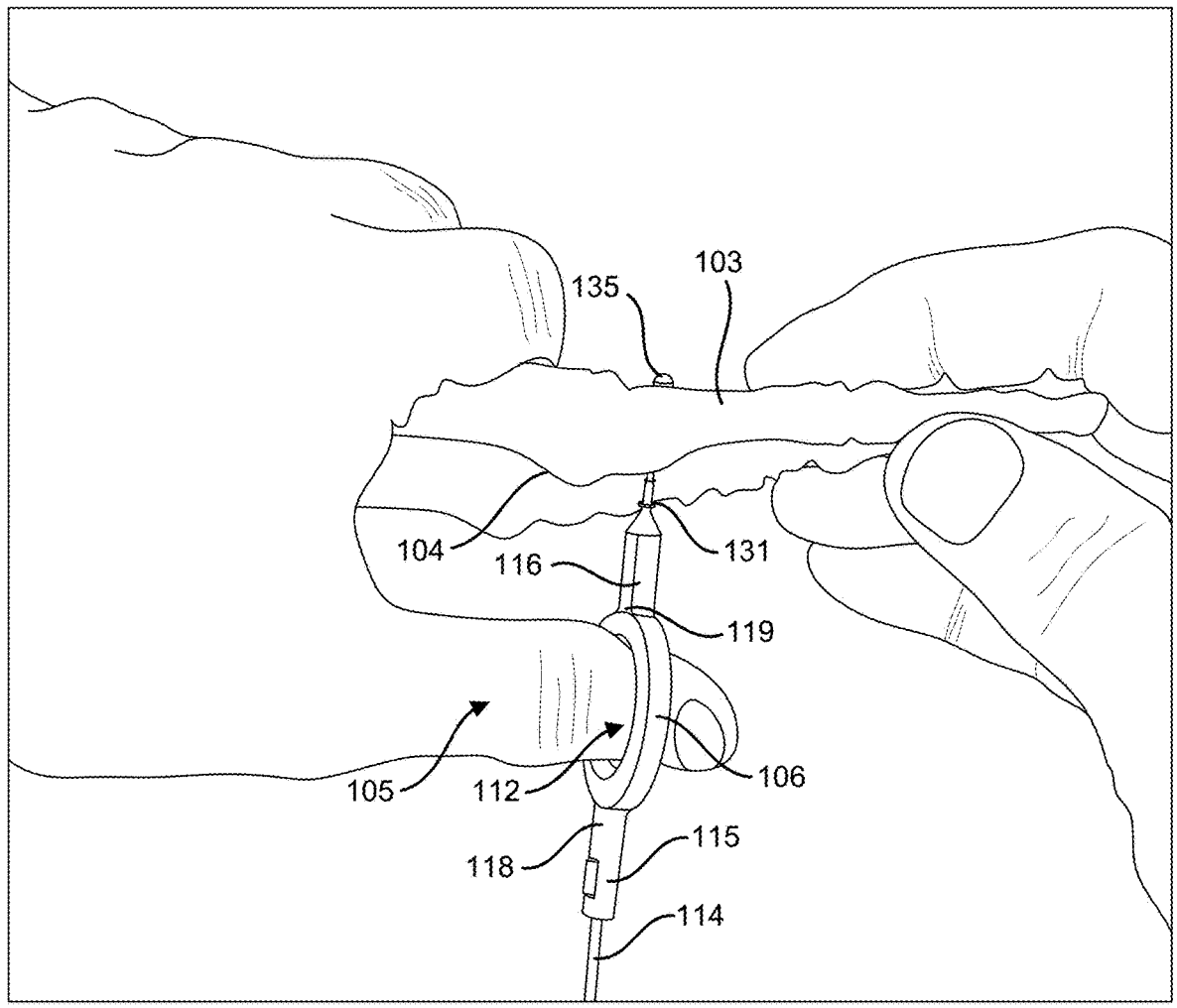
FIG. 42 illustrates a two-handed approach of implanting a soft tissue retention device comprising a bone anchor member and a soft tissue retention tack member utilizing the instrument of FIG. 36, in accordance with an aspect of the present disclosure.

The insertion and fixation portion 210 comprises a head portion 216 extending radially from another neck portion 219 situated at another side of the handle portion 206, as shown in FIGS. 36-42. In some embodiments, the neck portion 219 and the head portion 216 are arranged about 180° from the neck portion 218, base portion 215 and gauge rod 214. However, the instrument 215 may include other arrangements/orientations thereof. As shown in FIGS. 36 and 39-42, the head portion 216 includes a drive projection or tip 217 configured to temporarily engage a threaded and/or non-circular drive aperture of the implant, such as a soft tissue retaining portion or member thereof, for implantation and fixation (e.g., via application of a torque) of the implant. In one embodiment, the tip 217 and the aperture of the implant (e.g., the soft tissue retaining member) are threaded for threaded engagement therebetween (e.g., with a M1.25-0.3 thread). Other threads and/or connection configurations between the tip 217 and the aperture of the implant (e.g., the soft tissue retaining member) may be employed. The head portion 216 also provides another stop/seat surface to seat against or interface with the implant (e.g., the soft tissue retaining member thereof) and/or soft tissue and/or bone. When received on a user's digit (e.g., thumb as shown in FIG. 42), the handle portion 206 of the instrument 205 can easily rotate about the thumb for easy manual manipulation of the instrument 205 and selective usage of the gauge rod 214 or the tip 217.

FIGS. 37-42 illustrate an exemplary assembly and soft tissue retention device implantation procedure to fixedly attach, couple or retain soft tissue to a bone via a soft tissue retention device. By way of example, FIGS. 37-42 illustrate a method of use of the instrument 205 with respect to a non-cannulated (or partially-cannulated) soft tissue retention device and the attachment of a flexor digitorum longus tendon 204 to a plantar aspect of a proximal phalangeal base (bone) 200. However, use of the instrument 205 is applicable to other soft tissue (e.g., tendon or ligament) to bone attachment procedures, as well as other surgical procedures. The non- or partially-cannulated soft tissue retention device may comprise a soft tissue retention device disclosed in the '780 application, the '450 application, the '789 application, the '100 application and/or the '574 application. The exemplary assembly and soft tissue retention device implantation procedure may equally or similarly be employed to a fully cannulated soft tissue retention device, such as the soft tissue retention device 10 of FIGS. 1-7 described above.

FIG. 42 illustrates an exemplary manner of holding the instrument 205 during the procedure by placing one's thumb into/through the aperture 212 of the handle portion 206. Rotation of the instrument 205 about the user's thumb thereby allows one handed fixation and compression of the soft tissue retention implant.

Generally, as shown in FIGS. 37-42, the instrument 205 and the soft tissue retention implant can be utilized to affix, fix, secure, or otherwise hold soft tissue 204 (such as, but not limited to, a tendon) onto bone 200. In preparation of securing the soft tissue 204 to the bone 200 via the soft tissue retention implant, an aperture may be made in the soft tissue (e.g., pierced by a scalpel or other instrument) and a through hole or bore 201 formed (e.g., drilled) in the bone 200. A first member/portion of the soft tissue retention implant may be engaged with the head portion 216 of the instrument 205. A portion of the first member/portion may be translated through the aperture in the soft tissue 204 and into the bone through hole 201, and the soft tissue 204 appropriately tensioned (if desired). The first member/portion of the soft tissue retention implant may be compressed/forced against the soft tissue 204 to retain the relative position/orientation of the soft tissue 204 and the bone 200, such as via the instrument 205 and the user's hand (potentially the same hand that engages the instrument 205). A second member/portion of the soft tissue retention implant may be positioned within the bone through hole 201 from an opposing side thereof as compared to the first member/portion, and engaged with a torque tool. The second member/portion may be rotated with the torque tool, and the first member/portion prevented from rotating via the instrument 205, to threadably couple the first and second members/portions and fixedly retain the soft tissue 204 to the bone 200.

FIG. 37 illustrates determining a size of a soft tissue retention implant size (e.g., size of the soft tissue anchor member and/or size of the bone anchor member thereof) to use with the particular soft tissue/tendon 204 and bone 200, which may comprise gauging the height or thickness of the combined bone 200 and tendon 204. As shown in FIG. 37, after a through hole 201 has been formed (e.g., drilled) through the bone 200, the gauge rod portion 214 may be manually inserted through the tendon 204 and the through hole 201 until the bone 200 engages or comes into contact with the base portion 215 of the instrument 205, and the tendon 204 is slightly compressed. For example, the user may insert a digit (e.g., a thumb) through the aperture 212 of the handle portion 206 and wrap one or more other finger on the opposing side of the bone (e.g., the dorsal side).

As shown in FIG. 38, with the gauge rod portion 214 extending through the tendon 204 and the through hole 201, and the base portion 215 abutting, and potential compressing, the tendon 204 and/or bone 200, a gauge 220 may be received onto the exposed portion of the gauge rod portion 214. A lower sleeve portion 221 of the gauge 220 may include an aperture of the like such that the lower sleeve portion 221 is received over the rod portion 214 and contacts a top or opposing side or surface of the bone 200, as shown in FIG. 38. As also shown in FIG. 38, the gauge 220 may include a recess, opening or surface area 223 along within the rod portion 214 of the gauge 220 extends. The area 223 may include a plurality of visual and/or tactile indications 222 that form a size chart or otherwise indicate differing sized soft tissue retention devices/implants (or a component thereof). The position of the gauge rod tip 224 relative to the markings 222 of the gauge 220 (e.g., the marking 222 positioned closest to the tip 224) can thereby be utilized by the user to indicate the size of the tissue retention device/implant that corresponds to the size of the patient's bone 200 and/or tendon 204.

Figure 39:
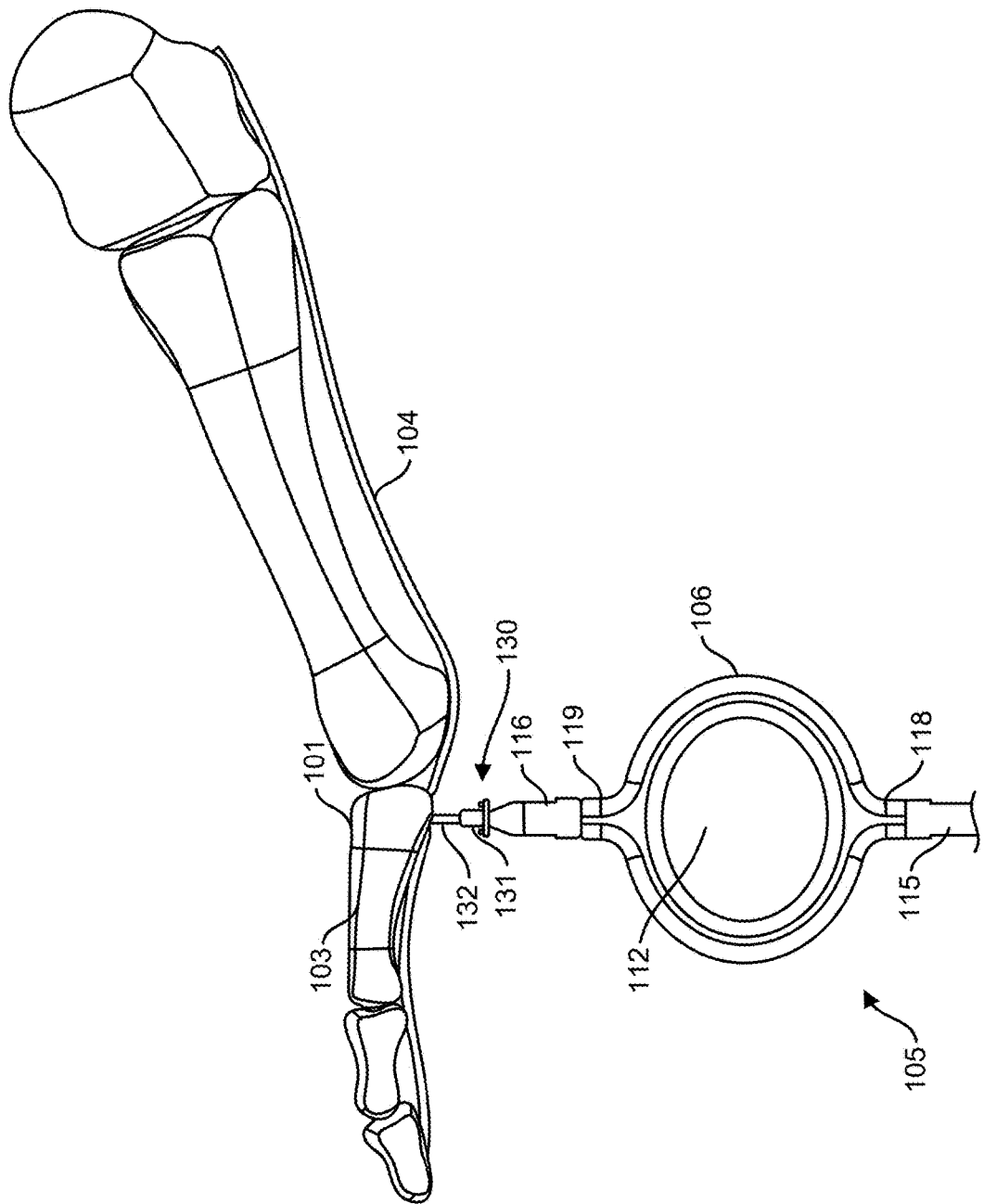
FIG. 39 illustrates the positioning of a soft tissue retention tack member of a soft tissue retention device through soft tissue and into a hole within a bone utilizing the instrument of FIG. 36, in accordance with an aspect of the present disclosure.

With the size of the soft tissue retention device/implant determined/gauged, the instrument 205 may then be utilized to install/implant the soft tissue retention device/implant by rotating the instrument 205 about the user's digit/finger (e.g., thumb) and removably coupled the drive tip 217 with a drive aperture or opening of a soft tissue retention tack member or portion 230 of the soft tissue retention device/implant. For example, the tip 217 may be threadably coupled with the drive aperture/opening of the soft tissue retention tack member 230. As shown in FIG. 39, the instrument 205 may then be utilized to insert the soft tissue retention tack member or portion 230 into the through hole 201 of the bone 200 and against the soft tissue/tendon 204. Thereafter, with the soft tissue retention tack member 230 removably coupled with the drive tip 217 of the head portion 216 of the instrument 205, a threaded stem portion 232 of the soft tissue retention tack member 230 may be held or maintained within the through hole 201 of the bone 200 (and/or a head portion of the soft tissue retention tack member 230 engaged/in abutment against the soft tissue/tendon 204) via one handed manipulation of the instrument 205 by the user (e.g., via a user's digit/finger (e.g., a thumb) extending through the aperture 212 of the handle portion 206 of the instrument 205).

With the soft tissue retention tack member 230 extending within the through hole 201 of the bone 200 and/or against the soft tissue/tendon 204, the soft tissue/tendon 204 may be compressed against the bone 200, as shown in FIG. 40. In some embodiments, the bone 200 and soft tissue/tendon 204 may be relatively arranged into a particular anatomical arrangement/configuration, and the instrument 205 used to force the soft tissue retention tack member 230 against the soft tissue/tendon 204, and thereby compress the soft tissue/tendon 204 between the soft tissue retention tack member 230 and the bone 200. For example, in some embodiments, the user may manually straighten the toe bone 200 of the patient's foot, and then force the soft tissue retention tack member 230 against the tendon 204, and thereby compress the tendon 204 between the soft tissue retention tack member 230 and the bone 200, to maintain the relative orientation of the toe bone 200 (after letting go of the toe bone 200), as shown in FIGS. 40 and 42. In such a configuration, the tendon 204 can be held in its desired location by compression of the instrument 205 via the user's hand and the hand of the user that engages the instrument 205 being wrapped around the patient's foot/toe bone 200 (i.e., a one-handed technique or method). Alternatively, the tendon 204 can be held in its desired location by compression of the instrument 205 via a user's hand and the other hand of the user engaging/forcing an opposing side of the patient's foot/toe bone 200 (i.e., a two-handed technique or method), as shown in FIG. 42.

FIG. 41 shows the compression of the soft tissue/tendon 204 against the bone 200 maintained by the user via the instrument 205 and the soft tissue retention tack member 230, a bone anchor member or portion 233 of the soft tissue retention device/implant may be positioned into the bone through hole 201 from an opposing side thereof relative to the soft tissue/tendon 204 and soft tissue retention tack member 230. As shown in FIG. 41, a threaded stem portion 234 of the bone anchor member 233 may be positioned within the through hole 201 of the bone 200, and a torque device or tool 250 may be engaged with a drive aperture or opening of a head portion 235 of the bone anchor member 233. The bone anchor member 233 may be rotated/torqued via the torque device 250 such that the threaded stem portion 234 of the bone anchor member 233 threadably engages, mates or couples with the threaded stem portion 232 of the soft tissue retention tack member 230 within the through hole 201 of the bone 200. Rotation of the soft tissue retention tack member 230 may be manually prevented (e.g., torque applied thereto) by the user via the engagement of the drive tip 231 of the instrument 205 with the drive aperture/opening of the head portion of the soft tissue retention tack member. Rotation of the bone anchor member 233 can thereby provide compression onto the soft tissue retention tack member to compress/force the soft tissue/tendon 204 onto the bone 200.

As may be recognized by those of ordinary skill in the art based on the teachings herein, numerous changes and modifications may be made to the above-described and other embodiments of the present disclosure without departing from the scope of the disclosure. The components of the instruments, guides, systems and related methods as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, systems and related methods (and components thereof) may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A device for retaining soft tissue to a bone, the device comprising:
   a first member comprising a first head portion and a first threaded shaft portion extending from an inner side of the first head portion, the first head portion and the first threaded shaft portion defining a cannulated opening that extends through the first member; and
   a second member comprising a second head portion and a second threaded shaft portion extending from an inner side of the second head portion, the second head portion and the second threaded shaft portion defining a cannulated opening that extends through the second member,
   wherein the inner side of the first head portion comprises a row of teeth and a plurality of through holes positioned between the first threaded shaft portion and the row of teeth that extend to an outer side of the first head portion that opposes the inner side thereof, and
   wherein the first and second threaded shaft portions are configured to threadably engage with each other.

2. The device of claim 1, wherein the outer side of the first head portion includes a first drive opening that is non-circular in cross-section, and wherein the cannulated opening of the first member is aligned with and extends from the first drive opening.

3. The device of claim 1, wherein the outer side of the first head portion includes a first drive opening that is non-circular in cross-section, and wherein the cannulated opening of the second member is aligned with and extends from the second drive opening.

4. The device of claim 1, wherein the first head portion comprises a convex outer surface profile.

5. The device of claim 1, wherein the second head portion comprises a convex outer surface profile.

6. The device of claim 1, wherein the teeth of the row of teeth of the inner side of the first head portion define axes that are aligned with an axis of the cannulated opening of the first member.

7. The device of claim 6, wherein an outer surface of the teeth of the row of teeth of the inner side of the first head portion are angled toward the axis of the cannulated opening of the first member as they extend to a tip of the teeth.

8. The device of claim 7, wherein an inner surface of the teeth of the row of teeth of the inner side of the first head portion are angled away from the axis of the cannulated opening of the first member as they extend from the inner surface to the tip of the teeth.

9. The device of claim 1, wherein the teeth of the row of teeth of the inner side of the first head portion taper as they extend from the inner surface to the tip of the teeth.

10. The device of claim 1, wherein the inner side of the first head portion comprises only a single row of teeth.

11. The device of claim 1, wherein the inner side of the first head portion is convex.

12. The device of claim 1, wherein the inner side of the second head portion is convex.

13. The device of claim 1, wherein the plurality of through holes are spaced about an axis of the cannulated opening of the first member.

14. The device of claim 1, wherein the first threaded post portion is externally threaded, and the cannulated opening of the second threaded post portion is internally threaded.

15. The device of claim 1, wherein the second threaded post portion is externally threaded, and the cannulated opening of the first threaded post portion is internally threaded.

16. The device of claim 1, wherein the first member is of one-piece construction.

17. The device of claim 1, wherein the second member is of one-piece construction.

18. The device of claim 1, wherein the inner side of the second head portion comprises a row of angled teeth extending about the second threaded shaft.

19. The device of claim 18, wherein the row of angled teeth of the inner side of the second head portion are angled in a direction extending about an axis of the cannulated opening of the second member that opposes a loosening direction of the threads of the first threaded shaft portion with respect to the second threaded shaft portion.

20. The device of claim 19, wherein an outer surface of the row of angled teeth of the inner side of the second head portion define the outer peripheral surface of the second head portion.

21. The device of claim 20, wherein the outer surface of the row of angled teeth of the inner side of the second head portion extend parallel to the axis of the cannulated opening of the second member.

22. The device of claim 18, wherein the row of angled teeth of the inner side of the second head portion extends about the periphery of the second head portion.

23. The device of claim 1, wherein the row of teeth of the inner side of the first head portion extends about the first threaded shaft.

24. The device of claim 1, wherein the row of teeth of the inner side of the first head portion extends about the periphery of the first head portion.

25. A method for securing soft tissue to a bone, comprising:
   forming an aperture in a portion of a soft tissue;
   forming a through aperture in a bone;
   obtaining the device of claim 1;
   extending the first threaded shaft portion of the first member of the device through the aperture in the soft tissue and into the through aperture of the bone with the inner side of the first head portion of the device in engagement with the soft tissue;
   extending the second threaded shaft portion of the second member of the device into the through aperture of the bone with the inner side of the second head portion of the device in engagement with the bone;
   threadably coupling the first and second shaft portions together within the through aperture of the bone; and
   compressing the first head member against the soft tissue and the second head member against the bone.

26. The method of claim 25, wherein extending the first threaded shaft portion of the first member of the device through the aperture in the soft tissue and into the through aperture of the bone with the inner side of the first head portion of the device in engagement with the soft tissue comprises mating a drive projection of a non-circular cross-section of an instrument the a first drive opening of the first head portion and manually positioning the first member relative to the bone via the instrument.

27. The method of claim 26, wherein extending the first threaded shaft portion of the first member of the device through the aperture in the soft tissue and into the through aperture of the bone with the inner side of the first head portion of the device in engagement with the soft tissue further comprises extending a gauge rod of the instrument that extends from the drive projection though the cannulated opening of the first member and translating the gauge rod through the aperture in the soft tissue and the through aperture of the bone.

28. The method of claim 27, further comprising extending a gauge over the gauge rod and against the bone such that a tip of the gauge rod is positioned proximate to one visual and/or tactile indication of a plurality of visual and/or tactile indications on the gauge, the plurality of visual and/or tactile indications representing a plurality of relative sizes of the device.

29. The method of claim 28, further comprising a plurality of the devices that correspond with the plurality of relative sizes of the device, wherein the plurality of the devices comprise a plurality of the first members with the first threaded shaft portions thereof being of differing lengths and/or a plurality of the second members with the second threaded shaft portions thereof being of differing lengths.

30. The method of claim 27, wherein threadably coupling the first and second shaft portions together within the through aperture of the bone comprises mating a drive projection of a torque tool with a second drive opening of the second head portion, position an end portion of the gauge rod within an opening of the torque tool extending from the drive projection thereof, rotating the first member via the torque tool, and preventing the second member from rotating via the instrument.

31. The method of claim 30, wherein preventing the second member from rotating via the instrument comprises manually engaging a handle portion of the instrument such that a finger extends through an aperture of the handle portion.

32. The method of claim 26, wherein the drive projection of the instrument extends from a first portion of a handle portion of the instrument, and wherein a gauge rod extends from a first portion of a handle portion of the instrument, and further comprising extending a gauge rod through the cannulated opening of the first member and translating the gauge rod through the aperture in the soft tissue and the through aperture of the bone.

33. The method of claim 32, further comprising extending a gauge over the gauge rod and against the bone such that a tip of the gauge rod is positioned proximate to one visual and/or tactile indication of a plurality of visual and/or tactile indications on the gauge, the plurality of visual and/or tactile indications representing a plurality of relative sizes of the device.

34. The method of claim 25, wherein compressing the first head member against the soft tissue and the second head member against the bone comprises forcing a plurality of portions of the soft tissue into the plurality of through holes of the first head portion.

35. A system for securing soft tissue to a bone, comprising:
   at least one device for retaining soft tissue to a bone comprising:
      a first member comprising a first head portion, a first threaded shaft portion extending from an inner side of the first head portion, and a cannulated opening that extends through the first head portion and the first threaded shaft portion; and
      a second member comprising a second head portion, a second threaded shaft portion extending from an inner side of the second head portion, and a cannulated opening that extends through the second head portion and the second threaded shaft portion,
      wherein the inner side of the first head portion comprises a row of teeth and a plurality of through holes positioned between the first threaded shaft portion and the row of teeth that extend to an outer side of the first head portion that opposes the inner side thereof, and
      wherein the first and second threaded shaft portions are configured to threadably engage with each other;
   a first instrument comprising a guide wire portion extending from a first drive projection provided at an end of a handle portion, wherein the guide wire portion is configured to extend through the cannulated openings of the first and second members of the device, and wherein the first drive projection is configured to mate with the first drive aperture of the first head member of the first member;

a second instrument comprising a handle portion, a second drive projection provided at an end of the handle portion, and an opening extending into the second drive projection configured to accept the guide wire portion of the first instrument therein, wherein the second drive projection is configured to mate with the second drive aperture of the second head member of the second member; and a sizing instrument comprising a through hole extending from a tip of the sizing instrument, a groove aligned with the through hole and a plurality of sizing markings proximate to the groove that correspond to differently sized second members of the device, wherein the through hole and the groove are configured to accept the guide wire portion of the first instrument therein.

36. The system of claim 35, wherein the at least one device comprises a plurality of the devices.

37. The system of claim 36, wherein the plurality of devices comprise a plurality of the first members with the first threaded shaft portions thereof being of differing lengths and/or a plurality of the second members with the second threaded shaft portions thereof being of differing lengths.

38. The system of claim 35, wherein the inner side of the second head portion of the at least one device comprises a row of angled teeth extending about the second threaded shaft.

39. The system of claim 38, wherein the row of angled teeth of the inner side of the second head portion of the at least one device extends about the periphery of the second head portion.

40. The system of claim 35, wherein the row of teeth of the inner side of the first head portion of the at least one device extends about the first threaded shaft.

41. The system of claim 35, wherein the row of teeth of the inner side of the first head portion of the at least one device extends about the periphery of the first head portion.

* * * * *